US005801015A

United States Patent [19]

Cottarel et al.

[11] Patent Number: 5,801,015

[45] Date of Patent: Sep. 1, 1998

[54] NUCLEIC ACID ENCODING A CANDIDA CELL CYCLE REGULATORY PROTEIN, TYP1 POLYPEPTIDE

[75] Inventors: Guillaume Cottarel, West Roxbury; Veronique Damagnez, Cambridge; Giulio Draetta, Winchester, all of Mass.

[73] Assignee: Mitotix, Inc., Cambridge, Mass.

[21] Appl. No.: 463,090

[22] Filed: Jun. 5, 1995

[51] Int. Cl.[6] .................. C12N 15/90; C12N 15/31; C12N 15/63; C07K 14/40

[52] U.S. Cl. .................. 435/69.1; 536/23.5; 435/325; 435/320.1; 435/196; 530/350

[58] Field of Search .................. 536/23.5, 23.74; 435/320.1, 69.1, 252.3, 196, 325; 935/66; 530/350

[56] References Cited

U.S. PATENT DOCUMENTS 5,441,880  8/1995  Beach et al. .................. 435/193

OTHER PUBLICATIONS

Kumagai et al. Cell 64: 903–914 (1991).
Russell, P. et al. Cell 57: 295–303 (1989).
Dunphy, W. et al. Cell 67: 189–196 (1991).
Goldberg, D. et al. Eur. J. Biochem. 213: 195–204 (1993).
Edgar, B.A. et al. Cell 57: 177–187 (1989).

*Primary Examiner*—Stephen Walsh
*Assistant Examiner*—Michael D. Pak
*Attorney, Agent, or Firm*—Foley, Hoag & Eliot LLP; Matthew P. Vincent; Beth E. Arnold

[57] ABSTRACT

The present invention relates to the discovery of novel cell cycle regulatory proteins from the human pathogen Candida.

20 Claims, 2 Drawing Sheets

NUCLEIC ACID ENCODING A CANDIDA CELL CYCLE REGULATORY PROTEIN, TYP1 POLYPEPTIDE

BACKGROUND OF THE INVENTION

The progression of a proliferating eukaryotic cell through the cell-cycle checkpoints is controlled by an array of regulatory proteins that guarantee that mitosis occurs at the appropriate time. Protein phosphorylation is the most common post-translational modification that regulates processes inside the cells, and a large number of cell cycle transitions are regulated by, in addition to protein-protein interactions, the phosphorylation states of various proteins. In particular, the execution of various stages of the cell-cycle is generally believed to be under the control of a large number of mutually antagonistic kinases and phosphatases. A paradigm for these controls is the CDC2 protein kinase, a cyclin-dependent kinase (CDK) whose activity is required for the triggering of mitosis in eukaryotic cells (for reviews, see Hunt (1989) Curr. Opin. Cell Biol. 1:268–274; Lewin (1990) Cell 61:743–752; and Nurse (1990) Nature 344:503–508). During mitosis, the CDC2 kinase appears to trigger a cascade of downstream mitotic phenomena such as metaphase alignment of chromosomes, segregation of sister chromatids in anaphase, and cleavage furrow formation. Many target proteins involved in mitotic entry of the proliferating cell are directly phosphorylated by the CDC2 kinase. For instance, the CDC2 protein kinase acts by phosphorylating a wide variety of mitotic substrates involved in regulating the cytoskeleton of cells, such that entry into mitosis is coordinated with dramatic rearrangement of cytoskeletal elements.

The CDC2 kinase is subject to multiple levels of control. One well-characterized mechanism regulating the activity of CDC2 involves the phosphorylation of tyrosine, threonine, and serine residues; the phosphorylation level of which varies during the cell-cycle (Krekk et al. (1991) EMBO J 10:305–316; Draetta et al. (1988) Nature 336:738–744; Dunphy et al. (1989) Cell 58:181–191; Morla et al. (1989) Cell 58:193–203, Gould et al. (1989) Nature 342:39–45; and Solomon et al (1990) Cell 63:1013–1024). The phosphorylation of CDC2 on Tyr-15 and Thr-14, two residues located in the putative ATP binding site of the kinase, negatively regulates kinase activity. This inhibitory phosphorylation of CDC2 is mediated at least in part by the weel and mikl tyrosine kinases (Russel et al. (1987) Cell 49:559–567; Lundgren et al. (1991) Cell 64:1111–1122; Featherstone et al. (1991) Nature 349:808–811; and Parker et al. (1992) PNAS 89:2917–2921). These kinases act as mitotic inhibitors, over-expression of which causes cells to arrest in the G2 phase of the cell-cycle. By contrast, loss of function of weel causes a modest advancement of mitosis, whereas loss of both wee1 and mik1 function causes grossly premature mitosis, uncoupled from all checkpoints that normally restrain cell division (Lundgren et al. (1991) Cell 64:1111–1122).

As the cell is about to reach the end of G2, dephosphorylation of the CDC2-inactivating Thr-14 and Tyr-15 residues occurs leading to activation of the CDC2 complex as a kinase. A stimulatory phosphatase, known as CDC25, is responsible for Tyr-15 and Thr-14 dephosphorylation and serves as a rate-limiting mitotic activator. (Dunphy et al. (1991) Cell 67:189–196; Lee et al. (1992) Mol. Biol. Cell. 3:73–84; Millar et al. (1991) EMBO J 10:4301–4309; and Russell et al. (1986) Cell 45:145–153). Recent evidence indicates that both the CDC25 phosphatase and the CDC2-specific tyrosine kinases are detectably active during interphase, suggesting that there is an ongoing competition between these two activities prior to mitosis (Kumagai et al. (1992) Cell 70:139–151; Smythe et al. (1992) Cell 68:787–797; and Solomon et al. (1990) Cell 63:1013–1024). This situation implies that the initial decision to enter mitosis involves a modulation of the equilibrium of the phosphorylation state of CDC2 which is likely controlled by variation of the rate of tyrosine dephosphorylation of CDC2 and/or a decrease in the rate of its tyrosine phosphorylation. A variety of genetic and biochemical data appear to favor a decrease in CDC2-specific tyrosine kinase activity near the initiation of mitosis which can serve as a triggering step to tip the balance in favor of CDC2 dephosphorylation (Smythe et al. (1992) Cell 68:787–797; Matsumoto et al. (1991) Cell 66:347–360; Kumagai et al. (1992) Cell 70:139–151; Rowley et al. (1992) Nature 356:353–355; and Enoch et al. (1992) Genes Dev. 6:2035–2046). Moreover, recent data suggests that the activated CDC2 kinase is responsible for phosphorylating and activating CDC25. This event would provide a self-amplifying loop and trigger a rapid increase in the activity of the CDC25 protein, ensuring that the tyrosine dephosphorylation of CDC2 proceeds rapidly to completion (Hoffmann et al. (1993) EMBO J. 12:53).

Although many fungal genera have been identified as etilogic opportunistic infections, it is known that Candida constitute the majority of the pathogens involved in these infections. Candida is unique among opportunistic pathogens because it is a resident fungus found in the normal flora of mucosa and skin of many animals, including humans. Although there are numerous species of Candida, the majority of infections are caused by C. albicans and C. tropicalis.

Clinical diagnosis and treatment of systemic fungemia suffers several shortcomings compared to bacterial septicemia. First, many of the approved antifungal therapeutics are more toxic to the patient than analogous antibacterial agents. As a result, clinicians desire a more reliable demonstration of fungemia before prescribing antifungal agents. Second, fungemic patients have a poor prognosis, unless diagnosed early in infection. Third, fungi generally grow slower than the major barceremic organisms, and consequently diagnosis requiring an in vitro culture step is time consuming. And fourth, some of the fungi (again in diagnosis requiring in vitro cultivation) will not yield colonies on synthetic media for weeks, if at all.

SUMMARY OF THE INVENTION

The present invention provides reagents and assays which permit rapid detection and evaluation of Candida yeast infections without employing culturing, incubation, subculturing or microscopic examination.

The present invention also makes available reagents and assays for identifying compounds which have antifungal properties and which may be used as anti-mycotic agents. Such agents developed with the subject assays can be used therapeutically, as well as, for example, preservatives in foodstuff, feed supplement for promoting weight gain in livestock, or in disinfectant formulations for treatment of non-living matter, e.g., for decontaminating hospital equipment and rooms.

In particular, the present invention relates to the discovery of novel cell-cycle regulatory proteins from animal pathogens, particularly from members of the genus Candida. One aspect of the invention features a Candida TYP I polypeptide, preferably a substantially pure preparation of a TYP1 polypeptide, or a recombinant TYP1 polypeptide. The TYP1 protein shares certain features which suggest that it is a homolog to the *S. Pombe* cdc25 phosphatase. In preferred embodiments, the biological activity of the polypeptide includes the ability to specifically bind a cyclin dependent kinase (CDK). Preferably, the TYP1 polypeptide has a phosphatase activity, e.g. a phosphotyrosine phosphatase activity, e.g. a phosphoserine/phosphothreonine phosphatase activity. The TYP1 polypeptide may also generally be characterized as having an amino acid sequence at least 60%, 80%, 90% or 95% homologous to the amino acid sequence in SEQ ID No: 7, in addition to those forms of the polypeptide which comprise an amino acid sequence identical to the polypeptide designated by SEQ ID No: 7. Preferred TYP1 polypeptides are at least 5, 10, 20, 50, 100, or 150 amino acids in length; e.g., the polypeptide comprises at least 5, preferably at least 10, more preferably at least 20, more preferably at least 50, 100, or 150 contiguous amino acids from SEQ ID No: 7. Moreover, the subject TYP1 polypeptides can either mimic (agonize) or inhibit (antagonize) the biological activity of the wild-type form of the phosphatase, e.g., of its ability to regulate Candida cell proliferation. In preferred embodiments, the TYP1 polypeptide is isolated or is a recombhinant form of a gene expressed by one of *Candida albicans, Candida stellatoidea, Candida tropicalis, Candida parapsilosis, Candida krusei, Candida pseudotropicalis, Candida quillermondii, Candida glabrata, Candida lusianiae,* or *Candida rugosa.*

Another aspect of the invention features a Candida CKS1 polypeptide, preferably a substantially pure preparation of a CKS1 polypeptide, or a recombinant CKS1 polypeptide. In preferred embodiments, the biological activity of the polypeptide includes the ability to specifically bind a cyclin dependent kinase (CDK). Preferably, the CKS1 polypeptide modulates the kinase activity of a CDK. The CKS1 polypeptide may generally be characterized as having an amino acid sequence at least 60%, 80%, 90% or 95% homologous to the amino acid sequence in SEQ ID No: 8, in addition to those forms of the polypeptide which comprise an amino acid sequence identical to the polypeptide designated by SEQ ID No: 8. Preferred CKS1 polypeptides are at least 5, 10, 20, 50 or 75 amino acids in length; e.g., the polypeptide comprises at least 5, preferably at least 10, more preferably at least 20, more preferably at least 50 or 75 contiguous amino acids from SEQ ID No: 8. Moreover, the subject CKS1 polypeptides can either mimic (agonize) or inhibit (antagonize) the biological activity of the wild-type form of the protein, e.g., of its ability to regulate Candida cell proliferation. In preferred embodiments, the CKS1 polypeptide is isolated from one of *Candida albicans, Candida stellatoidea, Candida tropicalis, Candida parapsilosis, Candida krusei, Candida pseudotropicalis, Candida quillermondii, Candida glabrata, Candida lusianiae,* or *Candida rugosa.*

Another aspect of the invention features a Candida CDK1 polypeptide, preferably a substantially pure preparation of a CDK1 polypeptide, or a recombinant CDK1 polypeptide. In preferred embodiments, the biological activity of the polypeptide includes the ability to specifically bind a cyclin. Preferably, the CDK1 polypeptide has an intrinsic kinase activity, which may depend on formation of a complex with a cyclin. The CDK1 polypeptide may generally be characterized as having an amino acid sequence at least 60%, 80%, 90% or 95% homologous to the amino acid sequence in SEQ ID No: 9, in addition to those forms of the polypeptide which comprise an amino acid sequence identical to the polypeptide designated by SEQ ID No: 9. Preferred CDK1 polypeptides are at least 5, 10, 20, 50, 100 or 150 amino acids in length; e.g., the polypeptide comprises at least 5, preferably at least 10, more preferably at least 20, more preferably at least 50, 100 or 150 contiguous amino acids from SEQ ID No: 9. Moreover, the subject CDK1 polypeptides can either mimic (agonize) or inhibit (antagonize) the biological activity of the wild-type form of the kinase, e.g., of its ability to regulate Candida cell proliferation. In preferred embodiments, the CDK1 polypeptide is isolated from one of *Candida albicans, Candida stellatoidea, Candida tropicalis, Candida parapsilosis, Candida krusei, Candida pseudotropicalis, Candida quillermondii, Candida glabrata, Candida lusianiae,* or *Candida rugosa.*

Another aspect of the invention features a Candida CYB1 polypeptide, preferably a substantially pure preparation of a CYB1 polypeptide, or a recombinant CYB1 polypeptide. In preferred embodiments, the biological activity of the polypeptide includes the ability to specifically bind a cyclin dependent kinase (CDK). Preferably, the CYB1 polypeptide modulates the kinase activity of a CDK. The CYB1 polypeptide may generally be characterized as having an amino acid sequence at least 60%, 80%, 90% or 95% homologous to the amino acid sequence in SEQ ID No: 10, in addition to those forms of the polypeptide which comprise an amino acid sequence identical to the polypeptide designated by SEQ ID No: 10. Preferred CYB1 polypeptides are at least 5, 10, 20, 50, 100 or 150 amino acids in length; e.g., the polypeptide comprises at least 5, preferably at least 10, more preferably at least 20, more preferably at least 50, 100 or 150 contiguous amino acids from SEQ ID No: 10. Moreover, the subject CYB1 polypeptides can either mimic (agonize) or inhibit (antagonize) the biological activity of the wild-type form of the protein, e.g., of its ability to regulate Candida cell proliferation. In preferred embodiments, the CYB1 polypeptide is isolated from one of *Candida albicans, Candida stellatoidea, Candida tropicalis, Candida parapsilosis, Candida krusei, Candida pseudotropicalis, Candida quillermondii, Candida glabrata, Candida lusianiae,* or *Candida rugosa.*

Another aspect of the invention features a Candida MOC1 polypeptide, preferably a substantially pure preparation of a MOC1 polypeptide, or a recombinant MOC1 polypeptide. In preferred embodiments, the biological activity of the polypeptide includes the ability to specifically bind a cyclin dependent kinase (CDK). Preferably, the MOC1 polypeptide has a kinase activity, e.g. a serine/theronine kinase activity. The MOC1 polypeptide may also generally be characterized as having an amino acid sequence at least 60%, 80%, 90% or 95% homologous to the amino acid sequence in SEQ ID No: 11, in addition to those forms of the polypeptide which comprise an amino acid sequence identical to the polypeptide designated by SEQ ID No: 11. Preferred MOC1 polypeptides are at least 5, 10, 20, 50, 100, or 150 amino acids in length; e.g., the polypeptide comprises at least 5, preferably at least 10, more preferably at least 20, more preferably at least 50, 100, or 150 contiguous amino acids from SEQ ID No: 11. Moreover, the subject MOC1 polypeptides can either mimic (agonize) or inhibit (antagonize) the biological activity of the wild-type form of the kinase, e.g., of its ability to regulate Candida cell proliferation. In preferred embodiments, the MOC1 polypeptide is isolated from one of *Candida albicans, Candida stellatoidea, Candida tropicalis, Candida parapsilosis, Candida krusei, Candida pseudotropicalis, Candida quillermondii, Candida glabrata, Candida lusianiae,* or *Candida rugosa.*

In yet other preferred embodiments, the subject regulatory proteins can be provided as recombinant fusion proteins which includes a second polypeptide portion, e.g., a second polypeptide having an amino acid sequence unrelated to a protein represented by one of SEQ ID Nos: 7–12, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Yet another aspect of the present invention concerns an immunogen comprising at least a portion of a polypeptide designated by one of SEQ ID Nos. 7–12 in an immunogenic preparation, the immunogen being capable of eliciting an immune response specific for the subject protein; e.g., a humoral response, e.g., an antibody response; e.g., a cellular response.

A still further aspect of the present invention features an antibody preparation specifically reactive with an epitope of one of the subject regulatory proteins.

Another aspect of the present invention provides a substantially pure nucleic acid having a nucleotide sequence which encodes one of the subject polypeptides. Furthermore, in certain preferred embodiments, the subject nucleic acids will include a transcriptional regulatory sequence, e.g. at least one of a transcriptional promoter or transcriptional enhancer sequence, operably linked to the recombinant gene sequence, e.g., to render the recombinant gene sequence suitable for use as an expression vector.

In yet a further preferred embodiment, the nucleic acid hybridizes under stringent conditions to a nucleic acid probe corresponding to at least 20 consecutive nucleotides of a gene designated by one of SEQ ID Nos: 1–6; more preferably it hybridizes to at least 40 consecutive nucleotides of one of SEQ ID Nos: 1–6; and even more preferably it hybridizes to at least 60, 90 or 120 consecutive nucleotides of one of SEQ ID Nos: 1–6.

In addition, the present invention makes available assays and reagents for identifying anti-proliferative agents, such as mitotic and meiotic inhibitors, which act by inhibiting biological action of one of the subject regulatory proteins. The subject assays include those designed to identify agents which disrupt binding to other regulatory proteins, as well as (if applicable) agents which function as inhibitors of the catalytic activity of the subject protein.

Other features and advantages of the invention will be apparent from the following detailed description, and from the claims. The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning, Volumes I and II* (D. N. Glover ed., 1985); *Oligonucleotide Synthesis (M. J. Gait ed.,* 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology, Vols.* 154 and 155 (Wu et al. eds.), *Immunochemical Methods In Cell And Molecular Biology* (Mayer and Walker, eds., Academic Press, London, 1987); *Handbook Of Experimental Immunology, Volumes I–IV* (D. M. Weir and C. C. Blackwell, eds., 1986).

DETAILED DESCRIPTION OF THE INVENTION

Figure 1A:
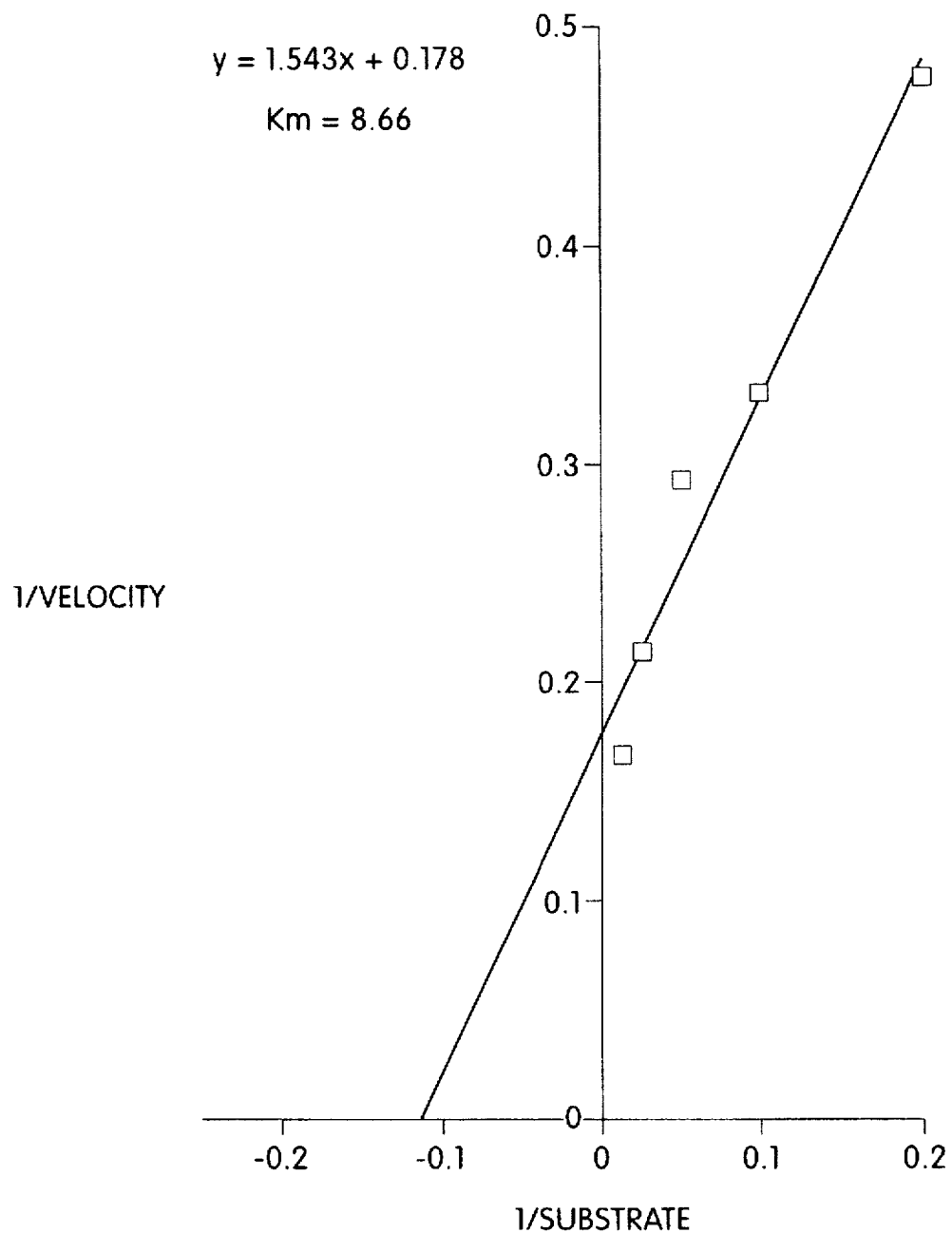
FIG. 1A demonstrates a Lineweaver-Burke analysis for recombinant Candida TYP1 hydrolysis of para-nitrophenylphospate.

Protein phosphorylation is the most common post-translational modification that regulates processes inside cells and plays a key role in regulating the cell cycle engine. Protein kinases add phosphates to proteins by transferring phosphate groups from, for example, ATP, to hydroxyl groups on amino acid side chains; protein phosphatases remove the phosphate group. Phosphorylation of a given amino acid in a protein can have a variety of effects: activating or inactivating a protein's enzymatic activity, or altering a protein's affinity for binding to other proteins. In dividing eukaryotic cells, circuits of regulatory kinases and phosphatases oversee both the initiation and completion of the major transitions of both the meiotic and mitotic cell-cycles. These regulatory networks guarantee that the successive events of each cell-cycle occur in a faithful and punctual manner. Passage of a cells through the cell cycle is regulated at a number of key control points. For example, mitosis cannot begin until the cell has grown sufficiently and replicated its genome accurately. Likewise, cell division cannot ensue until the mitotic spindle has distributed the chromosomes equally to both daughter cells.

In fission and budding yeasts, CDC2 (CDC28 in budding yeast) is the catalytic subunit of a protein kinase complex which is required for both DNA synthesis and for entry into mitosis. The timing and activation of the CDC2 kinase is regulated by a physical association with regulatory subunits called cyclins, as well as a network of protein kinases and phosphatases. For example, inhibitory phosphorylation of Tyr-15 and/or Thr-14 is mediated by the antagonistic actions of the Wee1 protein kinase and the CDC25 tyrosine phosphatase, the dephosphorylating activity of the latter resulting in activation a kinase activity of a CDC2/cyclin complex. Moreover, cyclins and cyclin dependent kinases (CDK), such as CDC2, are key components of the eukaryotic cell cycle in both unicellular and multicellular organisms, with similar allosteric control of CDKs existing amongst multicellular organisms.

The present invention derives from the discovery and isolation of genes encoding novel cell-cycle regulatory proteins from the human fungal pathogen Candida. One benefit provided by the present invention derives from the use of the subject proteins, antibodies and nucleic acids as reagents for diagnositic assays. Conventional diagnosis, as indicated above, often involves time-consuming steps for determining the presence of infection. Such delays can be unacceptable where prompt treatment must be accorded in order to provide positive prognosis. The subject diagnostic assays, particularly PCR-based procedures, can provide diagnostically relevant information in shorter time periods.

Furthermore, in light of the expected indespensible role of each of these proteins in control of cell proliferation, the present invention specifically contemplates drug screening assays which detect agents that disrupt the activity of one or more of the subject regulatory proteins, such as by disruption of binding to other cellular proteins or, where applicable, by inhibition of an enzymatic activity of the protein. Agents which inhibit the activation of Candida CDKs can be used as anti-fungal agents, such as to treat mycotic infections in animals, as preservatives in foodstuff, as a feed supplement for promoting weight gain in livestock, or in disinfectant formulations for decontaminanting equipment and rooms.

In particular, we have isolated from Candida genes which encode an apparent CDC25 phosphatase ("TYP1"), a p13$^{suc1}$ homolog ("CKS1"), a cyclin dependent kinase ("CDK1"), a cyclin ("CYB1"), a CDK-activating kinase catalytic subunit ("MOC1"), and a Map kinase kinase ("CMK1"). Each of these genes, while sharing some degree of homology with genes of other eukaryotes, are typically less than about 75 percent homologous with known genes, and many are less than 50 percent homologous with known genes. For convenience, Table 1 provides a guide to the relevant Sequence Listing entries which set forth the nucleic acid and amino acid sequences for the each of the subject regulatory genes.

TABLE 1

| Sequence Listing Guide | | |
|---|---|---|
| clone | nucleic acid sequence | amino acid sequence |
| TYP1 | SEQ ID No. 1 | SEQ ID No. 7 |
| CKS1 | SEQ ID No. 2 | SEQ ID No. 8 |
| CDK1 | SEQ ID No. 3 | SEQ ID No. 9 |
| CYB1 | SEQ ID No. 4 | SEQ ID No. 10 |
| MOC1 | SEQ ID No. 5 | SEQ ID No. 11 |
| CMK1 | SEQ ID No. 6 | SEQ ID No. 12 |

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding a polypeptide of the present invention, including both exon and (optionally) intron sequences. A "recombinant gene" refers to nucleic acid encoding such regulatory polypeptides, which may optionally include intron sequences which are either derived from a chromosomal DNA. Exemplary recombinant genes encoding the subject regulatory proteins are represented in SEQ ID Nos: 1–6. The term "intron" refers to a DNA sequence present in a given gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide of the present invention or where anti-sense expression occurs from the transferred gene, the expression of a naturally-occurring form of the protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors" In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the protein.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject polypeptides with a second amino acid sequence defining a domain foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "evolutionarily related to", with respect to nucleic acid sequences encoding each of the regulatory proteins, refers to nucleic acid sequences which have arisen naturally in an organism, including naturally occurring mutants. The term also refers to nucleic acid sequences which, while derived from naturally occurring genes, have been altered by mutagenesis, as for example, combinatorial mutagenesis described below, yet still encode polypeptides which have at least one activity of the wild-type ("authentic") protein.

The term "isolated" as also used herein with respect to nucleic acids, such as DNA or RNA, refers to molecules separated from other DNAs, or RNAs, respectively, that are present in the natural source of the macromolecule. For example, isolated nucleic acids encoding the subject polypeptides preferably include no more than 10 kilobases (kb) of nucleic acid sequence which naturally immediately flanks that gene in genomic DNA, more preferably no more than 5 kb of such naturally occurring flanking sequences, and most preferably less than 1.5 kb of such naturally occurring flanking sequence. The term isolated as used herein also refers to a nucleic acid or polypeptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of this invention pertains to an isolated nucleic acid comprising the nucleotide sequence encoding one of the subject regulatory proteins, biologically active fragments thereof, and/or equivalents of such nucleic acids. The term nucleic acid as used herein is intended to include such fragments and equivalents. Moreover, the term "nucleic acid encoding a TYP1 phosphate" is understood to include nucleotide sequences encoding homologous proteins functionally equivalent to the polypeptides Candida, TYP1 protein set forth in SEQ ID No. 7, or functionally equivalent polypeptides which, for example, retain a phosphatase activity, and which may additionally retain other activities of a TYP1 protein, e.g., the ability to bind to a CDK, e.g. a CDK1.

In similar fashion, the present invention contemplates nucleic acids which encode polypeptides that are homologous and functionally equivalent to other of the subject regulatory proteins. For instance, an equivalent polypeptide of CKS1 may retain the ability to bind to CDK1.

An equivalent polypeptide of CDK1 can retain the ability to bind to cyclins, such as CYB1, as well as MOC1 and the like, TYP1, CKS1 and/or other regulatory proteins, as well as cellular substrates of the authentic form of the kinase. In addition, an equivalent CDK1 polypeptide may retain its kinase activity. In similar fashion, an equivalent MOC1 polypeptide may be characterized by binding to CDK1 or another cyclin-dependent kinase, as well as, or alternatively, by its kinase activity towards substrates of the naturally occurring form of the protein. Equivalent polypeptides of the subject CYB1 protein will typically retain the ability to bind to a CDK, e.g. CDK1.

Moreover, it will be understood that such equivalent polypeptides as described above may mimic (agonize) the actions of the authentic form of one of the subject regulatory proteins. However, it is expressly provided that such equivalents include polypeptides which function to antagonize the normal function of the wild-type protein. For instance, dominant negative mutants of any of the enzymes TYP1, CDK1, MOC1 or CMK1 may competitively inhibit the function of the authentic protein by binding to substrate without catalytically acting upon it. Mutants of any of the subject proteins which produce non-productive complexes with other regulatory proteins can likewise be antagonistic homologs. Accordingly, the term "biological activity", with respect to homologs of the proteins enumerated in the Sequence Listing, refers to both agonism and antagonism of the ordinary function of the wild-type form of that protein.

Thus, equivalent nucleotide sequences will include sequences that differ by one or more nucleotide substitutions, additions or deletions, such as intragenus variants; and will also include sequences that differ from the nucleotide sequence encoding the portion of the a protein represented in one of SEQ ID Nos. 1–6 due to the degeneracy of the genetic code. Equivalent nucleic acids will also include nucleotide sequences that hybridize under stringent conditions (i.e., equivalent to about 20°–27° C. below the melting temperature ($T_m$) of the DNA duplex formed in about 1M salt) to a nucleotide sequence of a Candida gene represented in one of SEQ ID Nos. Nos. 1–6.

Preferred nucleic acids encode polypeptides comprising an amino acid sequence which is at least 60% homologous, more preferably 70% homologous and most preferably 80% homologous with an amino acid sequence shown in one of SEQ ID Nos. 7–12. Nucleic acids encoding polypeptides, particularly polypeptides retaining an activity of one of the subject regulatory proteins, and comprising an amino acid sequence which is at least about 90%, more preferably at least about 95%, and most preferably at least about 98–99% homologous with a sequence shown in one of SEQ ID Nos. 7–12 are also within the scope of the invention.

In yet a further embodiment, the recombinant regulatory genes may further include, in addition to the nucleic acid sequences shown in SEQ ID Nos. 1–6, additional nucleotide sequences. For instance, the recombinant gene can include nucleotide sequences of a PCR fragment generated by amplifying the gene from a genomic DNA library, e.g., intronic sequences, as well as 5' and 3' non-coding sequences of any of the subject genes.

Another aspect of the invention provides nucleic acid that hybridizes under high or low stringency conditions to nucleic acid which encodes a polypeptide identical or homologous with an amino acid sequence represented in one of SEQ ID Nos. 7–12. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding a Candida regulatory protein of the present invention, yet which differ from the nucleotide sequences shown in SEQ ID Nos. 1–6 due to degeneracy in the genetic code, are also within the scope of the invention. Such nucleic acids are understood to be capable of encoding functionally equivalent polypeptides (i.e., a polypeptide having at least a portion of the biological activity of a protein encoded by the enumerated sequences). For instance, a number of amino acids are designated by more than one triplet. Codons that specify the same amino acid (for example, CAU and CAC are synonyms for histidine) may result in "silent" mutations which do not affect the amino acid sequence of the protein. However, it is expected that DNA sequence polymorphisms that do lead to changes in the amino acid sequences of the protein will exist even within the same species. One skilled in the art will appreciate that these variations in one or more nucleotides (up to about 3–4% of the nucleotides) of a gene encoding a protein may exist among individual cells of a given species, e.g., amongst a population of C. albicans cells, due to natural allelic variation. Any and all such nucleotide variations and resulting amino acid polymorphisms are within the scope of this invention.

Fragments of the nucleic acid encoding portions of the subject regulatory proteins, such as the catalytic domain of the TYP1 phosphatase, are also within the scope of the invention. As used herein, such fragments refer to nucleotide sequences having fewer nucleotides than the coding sequence of the gene, yet still include enough of the coding sequence so as to encode a polypeptide with at least some of the activity of the full-length protein activity.

Nucleic acids within the scope of the invention may also contain linker sequences, modified restriction endonuclease sites and other sequences useful for molecular cloning, expression or purification of the recombinant polypeptides.

As indicated by the examples set out below, a nucleic acid encoding one of the subject proteins may be obtained from mRNA present in the cells of a pathogen from the genus Candida. It will also be possible to obtain nucleic acids encoding the subject proteins from genomic DNA obtained from such cells. For example, a gene encoding one of the pathogen regulatory proteins can be cloned from either a cDNA or a genomic library from other Candida species in accordance with protocols described herein, as well as those generally known in the art. For instance, a cDNA encoding a TYP1 protein can be obtained by isolating total mRNA from a culture of Candida cells, generating double stranded cDNAs from the total mRNA, cloning the cDNA into a suitable plasmid or bacteriophage vector, and isolating clones expressing TYP1 protein using any one of a number of known techniques, e.g., oligonucleotide probes or western blot analysis. Genes encoding related proteins can also be cloned using established polymerase chain reaction techniques in accordance with the nucleotide sequence information provided by the invention. The nucleic acid of the invention can be DNA or RNA.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding one of the subject regulatory proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes one of the regulatory proteins. Alternatively, the antisense construct is an oligonucleotide probe which is generated ex vivo and which, when introduced into the cell, causes inhibition of expression by hybridizing with the complementary mRNA and/or genomic sequences. In any event, it will be generally desirable to choose an antisense molecule which uniquely hybridizes to the Candida gene, e.g. does not hybridize under physiological conditions to DNA or RNA from a mammalian cell, especially a human cell. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of modes of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind, e.g. to provide a diagnostic screen for fungicemia. In particular, because of the significant difference in sequence between the subject Candida nucleic acids and apparent orthologs of other eukaryotes, even other single cell eukaryotes, the probe/primer of the present invention will permit diagnostic assays which can rapidly distinguish Candida infection from other causative agents of fungicemia.

This invention also provides expression vectors which include a nucleotide sequence encoding one of the subject polypeptides and operably linked to at least one regulatory sequence. Operably linked is intended to mean that the nucleotide sequence is linked to a regulatory sequence in a manner which allows expression of the nucleotide sequence. Regulatory sequences are art-recognized. Accordingly, the term regulatory sequence includes promoters, enhancers and other expression control elements. Exemplary regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the regulatory proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

This invention also pertains to a host cell transfected with a recombinant gene in order that it may express a recombinant protein of the present invention. The host cell may be any prokaryotic or eukaryotic cell. For example, a TYP1 protein of the present invention may be expressed in bacterial cells, such as E. coli, insect cells, yeast, or mammalian cells. Other suitable host cells are known to those skilled in the art. Exemplary cells genetically engineered to produce a recombinant protein of the present invention are the Schizosaccharomyces cells described below.

Another aspect of the present invention concerns recombinant forms of the subject Candida regulatory proteins. The term "recombinant protein" refers to a protein of the present invention which is produced by recombinant DNA techniques, wherein generally DNA encoding the protein is inserted into a suitable expression vector which is in turn used to transform a host cell to produce the heterologous protein. Moreover, the phrase "derived from", with respect to a recombinant gene encoding one of the subject proteins, is meant to include within the meaning of "recombinant protein" those proteins having an amino acid sequence of the native (or "authentic") form of the pathogen protein, or an amino acid sequence similar thereto, which is generated by mutation so as to include substitutions and/or deletions relative to a naturally occurring form of the protein. To illustrate, recombinant proteins preferred by the present invention, in addition to those having an amino acid sequence of the native proteins, are those recombinant proteins having amino acid sequences which are at least 70% homologous, more preferably 80% homologous and most preferably 90% homologous with an amino acid sequence shown in one of SEQ ID Nos: 7–12. A polypeptide which having an amino acid sequence that is at least about 95%, more preferably at least about 98%, and most preferably identical to one of the sequences shown in SEQ ID Nos: 7–12 are also within the scope of the invention. Thus, the present invention pertains to recombinant proteins which are derived from Candida and which have amino acid sequences evolutionarily related to a protein represented by any one of SEQ ID Nos: 7–12, wherein "evolutionarily related to" refers to polypeptides having amino acid sequences which have arisen naturally (e.g. by allelic variance or by differential splicing), as well as mutational variants of the regulatory proteins which are derived, for example, by combinatorial mutagenesis.

The present invention further pertains to methods of producing the subject polypeptides. For example, a host cell transfected with a nucleic acid vector directing expression of a nucleotide sequence encoding one of the subject regulatory proteins can be cultured under appropriate conditions to allow expression of the polypeptide to occur. The polypeptide may be secreted and isolated from a mixture of cells and medium containing the recombinant protein. Alternatively, the polypeptide may be retained cytoplasmically and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for the recombinant protein. In a preferred embodiment, the regulatory protein is a fusion protein containing a domain which facilitates its purification, such as a GST fusion protein.

Thus, a nucleotide sequence derived from the cloning of one of the subject proteins, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known intracellular proteins, e.g., p53, RB, p16, human TYP1, and the like. Similar procedures, or modifications thereof, can be employed to prepare recombinant forms of the subject proteins, or portions thereof, by microbial means or tissue-culture technology in accord with the subject invention.

Recombinant forms of the subject regulatory proteins can be produced by ligating the cloned gene, or a portion thereof, into a vector suitable for expression in either prokaryotic cells, eukaryotic cells, or both. Expression vehicles for production of the recombinant proteins include plasmids and other vectors. For instance, suitable vectors for the expression of the recombinant protein include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, pRS vectors, e.g., pRS303, pRS304, pRS305, pRS306, etc., are cloning and expression vehicles useful in the introduction of genetic constructs into S. cerevisiae (see, for example, Sikorski et al. (1989) Genetics 122:19–27; and Christianson (1992) Gene 110:119–122). These vectors can replicate in E. coli due to the presence of the pBR322 ori, and in S. cerevisiae due to the replication determinant of the yeast 2 micron plasmid. In addition, drug resistance markers such as ampicillin can be used. Expression in other yeast systems, such as P. pastoris, is contemplated by this invention.

In some instances, it may be desirable to express the recombinant genes by the use of a baculovirus expression system. Examples of such baculovirus expression systems include pVL-derived vectors (such as pVL1392, pVL1393 and pVL941), pAcUW-derived vectors (such as pAcUWI), and pBlueBac-derived vectors (such as the β-gal containing pBlueBac III, p2Blue). Further, the p2Blue vector has the added feature of being capable of expressing two exogenous proteins simultaneously (p2Blue, Invitrogen Corp. Catalog number V-1970-10).

When expression of a carboxy-terminal portion of one of the polypeptides enzyme is desired, i.e., a truncated form of the protein, it may be desirable to add a start codon (ATG)

to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing recombinantly-derived polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene so as to be covalently linked in-frame with a second nucleotide sequence encoding a different polypeptide. This type of expression system can be useful, for instance, where it is desirable to produce an immunogenic fragment of the protein. For example, the VP6 capsid protein of rotavirus can be used as an immunologic carrier protein for portions of the TYP1 polypeptide, either in the monomeric form or in the form of a viral particle. The nucleic acid sequences corresponding to the portion of the protein to which antibodies are to be raised can be incorporated into a fusion gene construct which includes coding sequences for a late vaccinia virus structural protein to produce a set of recombinant viruses expressing fusion proteins comprising a portion of the TYP1 protein as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a TYP1 protein and the poliovirus capsid protein can be created to enhance immunogenicity of the set of polypeptide antigens (see, for example, EP Publication No. 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized, wherein a desired portion of a one of the subject proteins is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of the subject proteins can also be expressed and presented by bacterial cells.

In addition to utilizing fusion proteins to enhance immunogenicity, it is widely appreciated that fusion proteins can also facilitate the expression of proteins. For example, recombinant forms of each of the subject pathogen proteins can be generated as glutathione-S-transferase (GST) fusion proteins. Such GST fusion proteins can be used to simplify purification of the protein, such as through the use of glutathione-derivatized matrices (see, for example, *Current Protocols in Molecular Biology*, eds. Ausabel et al. N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, can facilitate purification of the fusion protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausabel et al. John Wiley & Sons: 1992).

The present invention also makes available purified, or otherwise isolated forms of the subject fungal proteins, which are isolated from, or otherwise substantially free of, other intracellular proteins which may be normally associated, especially other cell-cycle regulatory proteins. The term "substantially free of other cellular proteins" (also referred to herein as "contaminating proteins") is defined as encompassing, for example, protein preparations comprising less than 20% (by dry weight) contaminating protein, and preferably comprises less than 5% contaminating protein. Purified forms of the subject polypeptides can be prepared as purified preparations, for example, by using the cloned genes as described herein. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

However, the subject polypeptides can also be provided in pharmaceutically acceptable carriers for formulated for a variety of modes of administration, including systemic and topical or localized administration. Techniques and formulations generally may be found in Remmington's Pharmaceutical Sciences, Meade Publishing Co., Easton, Pa. In an exemplary embodiment, a dominant negative mutant of one of the subject regulatory proteins can be provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

Another aspect of the invention related to polypeptides derived from the full-length forms of the subject proteins. Isolated peptidyl portions can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, TYP1 can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of, for example, CDK activation, such as by microinjection assays. In an illustrative embodiment, peptidyl portions of the Candida TYP1 can be tested for CDK-binding activity, as well as inhibitory ability, by expression as, for example, thioredoxin fusion proteins, each of which contains a discrete fragment of the TYP1 protein (see, for example, U.S. Pat. Nos. 5,270,181 and 5,292,646; and PCT publication WO94/02502).

It is also possible to modify the structure of the subject regulatory proteins for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered finctional equivalents of the polypeptides described in more detail herein. Such modified polypeptides can be produced, for instance, by amino acid substitution, deletion, or addition.

Moreover, it is reasonable to expect that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic =glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur-containing=cysteine and methionine. (see, for example, Biochemistry, 2nd ed, Ed. by L. Stryer, WH Freeman and Co.: 1981). Whether a change in the amino acid sequence of a peptide results in a finctional homolog of one of the subject proteins can be readily determined by assessing the ability of the variant peptide to produce a response in cells in a fashion similar to the wild-type protein, or by evaluating the homolog in an in vitro system. Polypeptides in which more than one replacement has taken place can readily be tested in the same manner.

This invention further contemplates a method of generating sets of combinatorial mutants of the subject proteins, as well as truncation mutants, and is especially useful for identifying functional variant sequences. One purpose for generating and screening such combinatorial libraries is, for example, to isolate homologs from the library which function in the capacity as one of either an agonists or an antagonist of the biological activities of the authentic protein, or alternatively, which possess novel biological activities all together. To illustrate, TYP1 homologs can be engineered by the present method to provide homologs which lack phosphatase activity yet still retain the ability to bind to a CDK, e.g., a CDK1 binding capacity, or which bind to other cell-cycle proteins and prevent the action of the naturally occurring form of the protein. Such mutants can therefore be dominant negative phenotypes of the subject pathogen TYP1 enzyme, and can be used in, for example, gene therapy protocols that target delivery of a recombinant gene encoding a dominant negative TYP1 mutant to a pathogen.

For example, a combinatorial TYP1 library is produced by way of a degenerate library of genes encoding a library of polypeptides which each include at least a portion of potential TYP1 nucleotide sequences. A mixture of synthetic oligonucleotides can be enzymatically ligated into gene sequences such that the degenerate set of TYP1 nucleotide sequences are expressible as individual polypeptides, or alternatively, as a set of larger fusion proteins (e.g., for phage display) containing the TYP1 sequence library therein. In an illustrative embodiment, the library of TYP1 phosphatase mutants is expressed in the S. pombe cdc25–22, weel-50 strain described below. Co-expression of the wild-type TYP1 (e.g. a recombinantly produced TYP1 from Candida, with a member of the TYP1 variant library, in conjunction with detecting proliferation of the cells, will permit the identification of dominant negative TYP1 mutants which are able to rescue the otherwise hyper-mitotic cell.

There are many ways by which the library of TYP1 homologs can be generated from a degenerate oligonucleotide sequence. For instance, chemical synthesis of a degenerate gene sequence can be carried out in an automated DNA synthesizer, and the synthetic genes then ligated into an appropriate gene for expression. The purpose of a degenerate set of TYP1 oligonucleotide sequences is to provide, in one mixture, all of the sequences encoding the desired set of potential TYP1 sequences. The synthesis of degenerate oligonucleotides is well known in the art (see, for example, Narang, SA (1983) *Tetrahedron* 39:3; Itakura et al. (1981) *Recombinant DNA, Proc 3rd Cleveland Sympos. Macromolecules,* ed. AG Walton, Amsterdam: Elsevier polypeptide273–289; Itakura et al. (1984) *Annu. Rev. Biochem.* 53:323; Itakura et al. (1984) *Science* 198:1056; Ike et al. (1983) *Nucleic Acid Res.* 11:477). Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Moreover, there are several forms of mutagenesis generally applicable, in addition to a general combinatorial mutagenesis approach. For example, homologs of the subject proteins (both agonist and antagonist forms) can be generated and screened using, for example, alanine scanning mutagenesis and the like (Ruf et al. (1994) *Biochemistry* 33:1565–1572; Wang et al. (1994) *J Biol Chem* 269:3095–3099; Balint et al. (1993) *Gene* 137:109–118; Grodberg et al. (1993) *Eur J Biochem* 218:597–601; Nagashima et al. (1993) *J Biol Chem* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol Cell Biol* 12:2644–2652; McKnight et al. (1982) *Science* 232:316); or by saturation mutagenesis (Meyers et al (1986) *Science* 232:613). Such techniques will be generally understood to provides for reduction of the subject regulatory proteins to generate mimetics, e.g. peptide or non-peptide agents, which are able to disrupt binding of a naturally-occurring form of a protein of the present invention with other cell-cycle regulatory proteins of the pathogen from which it was derived, e.g. disrupts the binding of the pathogen TYP1 to a CDK.

Thus, such mutagenic techniques as described above are particularly useful to map the determinants of the subject proteins which participate in protein-protein interactions. To illustrate, the critical residues of a TYP 1 protein which are involved in molecular recognition of a cyclin-dependent kinase, such as CDK 1, can be determined and used to generate TYP 1-derived peptidomimetics which competitively inhibit binding of the phosphatase with the CDK (see, for example, "Peptide inhibitors of human papillomavirus protein binding to retinoblastoma gene protein" European patent applications EP-412,762A and EP-B31,080A). By employing, for example, scanning mutagenesis to map the amino acid residues of one of the subject TYP1 involved in binding E6, peptidomimetic compounds (e.g. diazepine or isoquinoline derivatives) can be generated which mimic those residues in binding to CDK, and which therefore can inhibit binding of authentic TYP 1 to CDK and thereby interfere with the function of TYP1 and/or the Kinase in proliferation of the pathogen. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted γ-lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71). In similar fashion, mimetics can be designed which bind to any of the other subject regulatory proteins, or mimic their binding to other proteins.

Another aspect of the invention pertains to antibodies and antibody preparations specifically reactive with at least one of the subject proteins. For example, by using peptides based on the cDNA sequence of one of the proteins represented in SEQ ID Nos. 7–12, anti-protein/anti-peptide antisera or monoclonal antibodies can be made using standard methods. A mammal such as a mouse, a hamster or rabbit, can be immunized with an immunogenic form of the peptide. Techniques for conferring immunogenicity on a protein or peptide include conjugation to carriers or other techniques well known in the art. An immunogenic form of the protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of one of the pathogen-derived proteins of the present invention, e.g. antigenic determinants of a protein represented by one of SEQ ID Nos. 7–12 or a closely related homolog (e.g. 90 percent homologous, more preferably at least 95 percent homologous). In yet a further preferred embodiment of the present invention, antibodies do not substantially cross react (i.e. do not react specifically) with a protein which is: e.g. less than 90 percent homologous, more preferably less than 95 percent homologous, and most preferably less than 98–99 percent homologous with one of SEQ ID Nos. 7–12. By "not substantially cross react", it is meant that the antibody has a binding affinity for a nonhomologous protein, particularly orthologous proteins from mammalian cells, which is at least one order of magnitude, more preferably at least two orders of magnitude, and even more preferably at least three orders of magnitude less than the binding affinity of that antibody for one of the proteins of SEQ ID Nos. 7–12.

An effective amount of a conjugate-containing composition is introduced into a host animal such as a goat, rabbit, mouse, rat, horse or the like to induce the production (secretion) of antibodies to the polypeptide. Effective amounts of immunogens useful for inducing antibody secretions in host animals are well known in the art. Methods of introduction into the host animal are also well known and are typically carried out by parental administration as by injection. A plurality of such introductions is normally utilized so that the host is hyperimmunized to the immunogenic polypeptide-containing conjugate. For example, weekly introductions over a one-to-two-month time period can be utilized until a desired anti-polypeptide antibody titer is achieved.

Following immunization antisera can be obtained and, if desired, polyclonal antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. polypeptide. 77–96). Hybridoma cells can be screened immunochemically for production of antibodies specifically reactive with the immunogen and monoclonal antibodies isolated from a culture comprising such hybridoma cells.

The term antibody as used herein is intended to include fragments thereof which are also specifically reactive with one of the subject proteins. Antibodies can be fragmented using conventional techniques and the fragments screened for utility in the same manner as described above for whole antibodies. For example, F(ab')$_2$ fragments can be generated by treating a full antibody with pepsin. The resulting F(ab')$_2$ fragment can be treated to reduce disulfide bridges to produce Fab' fragments. The antibody of the present invention is further intended to include bispecific and chimeric molecules.

An antibody preparation of this invention prepared from a polypeptide as described above can be in dry form as obtained by lyophilization. However, the antibodies are normally used and supplied in an aqueous liquid composition in serum or a suitable buffer such as PBS.

Both monoclonal and polyclonal antibodies (Ab) directed against one of the subject regulatory proteins, and antibody fragments such as Fab' and F(ab')$_2$, can be used to block the action of that protein and allow the study of its role in the cell-cycle or in cell proliferation. Moreover, such antibodies can also be used diagnostically to detect an infection involving Candida.

Moreover, the nucleotide sequence determined from the cloning of the subject regulatory proteins will permit the generation of probes designed for use in identifying the presence of a Candida infection such as an infection involving C. albicans. For instance, the present invention provides a probe/primer comprising a substantially purified oligonucleotide, wherein the oligonucleotide comprises a region of nucleotide sequence which hybridizes under stringent conditions to at least 10, more preferably 25, 50, or 100 consecutive nucleotides of sense or anti-sense sequence of one of SEQ ID Nos: 11-6, or naturally occurring mutants thereof. In preferred embodiments, the probe/primer further comprises a label group attached thereto and able to be detected, e.g. the label group is selected from the group consisting of radioisotopes, fluorescent compounds, enzymes, and enzyme co-factors. Such probes can be used as a part of a diagnostic test kit for identifying and phenotyping particular mycotic infections, such as in a sample of cells from a patient, or in a foodstuff, or on equipment.

The present invention also provides assays and reagents for identifying anti-fungal and anti-parasitic agents, e.g. agents which act to inhibit proliferation of a pathogen by altering the activity of one or more of the subject pathogen proteins. To illustrate, inhibitors of the Candida TYP1 phosphatase can be used in the treatment of candidiasis- an opportunistic infection that commonly occurs in debilitated and immunosuppressed patients. TYP1 inhibitors could be used to treat these infections in patients with leukemias and lymphomas, in people who are receiving immunosuppressive therapy, and in patients with such predisposing factors as diabetes mellitus or AIDS, where fungal infections are a particular problem. TYP1 inhibitors can be generated for treatment of mycotic infections caused by, for example, *Candida albicans, Candida stellatoidea, Candida tropicalis, Candida parapsilosis, Candida krusei, Candida pseudotropicalis, Candida quillermondii, Candida glabrata, Candida lusianiae,* or *Candida rugosa*. Anti-proliferative agents developed with the subject assays can also be used, for example, as preservatives in foodstuff, as a feed supplement for promoting weight gain in livestock, or in disinfectant formulations for treatment of non-living matter, e.g., for decominating hospital equipment and rooms. Furthermore, as a result of the considerable divergence between TYP1 proteins, it is likely that differential screening assays, e.g. side-by-side comparison of inhibition of human TYP1 relative to one of the Candida TYP1 enzyme, can be used to identify agents that exhibit specific inhibitory effects directed at the form of the subject TYP1 protein present in the pathogen, without substantially inhibiting a CDC25 phosphatase in human or other animal cells. Thus, by making available purified and recombinant proteins, the present invention facilitates the development of assays which can be used to screen for drugs which are either agonists or antagonists of the normal cellular function of the subject regulatory proteins. An inhibitor, as identified in the subject assays, is an agent which is able to cause a statistically significant decrease in one or more proliferative activities of a regulatory protein of the present invention.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target, as may be manifest in an alteration of binding affinity between one of the subject proteins and other proteins with which they interact, in changes in enzymatic activity of one of the subject proteins, or in changes in a property of the molecular target manifest from binding to one of the regulatory proteins.

Accordingly, in an exemplary screening assay of the present invention, the compound of interest is contacted with an isolated and purified TYP1 polypeptide which is ordinarily capable of binding a cyclin-dependent kinase. To the mixture of the compound and TYP1 polypeptide is then added a composition containing a CDK polypeptide. Detection and quantification of CDK/TYP1 complexes provides a means for determining the compound's efficacy at inhibiting (or potentiating) complex formation between the CDK and TYP1 polypeptides. The efficacy of the compound can be assessed by generating dose response curves from data obtained using various concentrations of the test compound. Moreover, a control assay can also be performed to provide a baseline for comparison. In the control assay, an isolated and purified CDK is added to a composition containing the TYP1 protein, and the fonnation of CDK/TYP1 complexes is quantitated in the absence of the test compound. Efficacy of an agent is based on producing a statistically significant change in formation of such complexes relative to the control. It will be understood that, in general, the order in which the reactants may be admixed can be varied, and can be admixed simultaneously.

Complex formation between the TYP1 polypeptide and CDK polypeptide may be detected by a variety of techniques. For instance, modulation of the formation of complexes can be quantitated using, for example, detectably labeled proteins such as radiolabelled (e.g. $^{32}$P, $^{35}$S, $^{14}$C or $^{3}$H), fluorescently labeled (e.g. FITC), or enzymatically labeled polypeptides, by immunoassay, or by chromatographic detection. The use of enzymatically labeled TYP1 or CDK proteins will, of course, generally be used only when enzymatically inactive portions of those proteins are used, as each protein can possess a measurable intrinsic activity which can be detected.

Typically, it will be desirable to immobilize one of the two polypeptides to facilitate separation of complexed from uncomplexed forms of one or both of the proteins, as well as to accommodate automation of the assay. Binding of the CDK to TYP1, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/TYP1 (GST/TYP1) fusion proteins can be adsorbed onto glutathione sepharose beads (Sigma Chemical, St. Louis, Mo.) or glutathione derivatized microtitre plates, which are then combined with the CDK polypeptide, e.g. an $^{35}$S-labeled CDK polypeptide, and the test compound, and the mixture incubated under conditions conducive to complex formation, e.g. at physiological conditions for salt and pH, though slightly more stringent conditions may be desired, e.g., at 4° C. in a buffer containing 0.6M NaCl or a detergent such as 0.1% Triton X-100. Following incubation, the beads are washed to remove any unbound CDK polypeptide, and the matrix immobilized radiolabel determined directly (e.g. beads placed in scintillant), or in the supernatant after the protein complexes are subsequently dissociated. Alternatively, the complexes can dissociated from the matrix, separated by SDS-PAGE, and the level of labeled polypeptide found in the bead fraction quantitated from the gel using standard electrophoretic techniques such as described in the appended examples.

Other techniques for immobilizing proteins on matrices are also available for use in the subject assay. For instance, either of the proteins can be immobilized utilizing conjugation of biotin and streptavidin. For instance, biotinylated TYP1 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the TYP1 but which do not interfere with CDK binding can be derivatized to the wells of the plate, and the TYPL polypeptide trapped in the wells by antibody conjugation. As above, preparations of a CDK polypeptide and a test compound are incubated in the TYP1 presenting wells of the plate, and the amount of protein complex trapped in the well can be quantitated. Exemplary methods for detecting such complexes, in addition to those described above for the GST-immobilized complexes, include immunodetection of complexes using antibodies reactive with the CDK polypeptide, or which are reactive with the TYP1 protein and compete for binding with the CDK polypeptide; as well as enzyme-linked assays which rely on detecting an enzymatic activity associated with the CDK polypeptide (instead of the intrinsic activity). In the instance of the latter, the enzyme can be chemically conjugated or provided as a fusion protein with a CDK polypeptide. To illustrate, a CDK1 polypeptide can be chemically cross-linked or genetically fused with horseradish peroxidase, and the amount of CDK1 trapped in the complex with TYP1 can be assessed with a chromogenic substrate of the exogenous enzyme, e.g. 3,3'-diamino-benzadine terahydrochloride or 4-chloro-1-napthol. Likewise, a fusion protein comprising the CDK and glutathione-S-transferase can be provided, and complex formation quantitated by detecting the GST activity using 1-chloro-2,4-dinitrobenzene (Habig et al (1974) *J Biol Chem* 249:7130).

As alluded to above, intrinsic enzymatic activities can be relied upon to detect the efficacy of an agent against TYP1. The detection of the TYP1 phosphatase activity is described in more detail below. However, the downstream targets of TYP1, such as a CDK, may also have an intrinsic activity which can be utilized to quantitate the interaction with TYP1. In an exemplary embodiment, an enzymatically active TYP1 is contacted with a phosphorylated CDK/cyclin complex, e.g. CDK1/CYB1, under conditions wherein, absent an inhibitor of the TYP1, that enzyme would dephosphorylate and activate the CDK/cyclin complex. Activation could be detected by conversion of a substrate for the kinase complex, such as phosphorylation of a histone HI protein with $^{32}$P-labeled phosphate.

For processes which rely on immunodetection for quantitating one of the proteins trapped in the complex, antibodies against the protein, such as either anti-CDK or anti-TYP1 antibodies, can be used. Alternatively, the protein to be detected in the complex can be "epitope tagged" in the form of a fusion protein which includes, in addition to the CDK polypeptide or TYP1 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) whi ch includes a 10-residue sequence from c-myc, as well as the pFLAG system (International Biotechnologies, Inc.) or the pfZZ-protein A system (Pharamacia, N.J.).

Moreover, the subject polypeptides can be used to generate an interaction trap assay, as described in the examples below (see also, U.S. Pat. No. 5,283,317; Zervos et al. (1993) *Cell* 72:223–232; Madura et al. (I1993) *J Biol Chem* 268:12046–12054; Bartel et al. (1993) *Biotechniques* 14:920–924; and Iwabuchi et al (1993) *Oncogene* 8:1693–1696), for subsequently detecting agents which disrupt binding of TYP1 to a CDK or other cell-cycle regulatory protein, such as a cyclin.

The interaction trap assay relies on reconstituting in vivo a functional transcriptional activator protein from two separate fusion proteins, one of which comprises the DNA-binding domain of a transcriptional activator fused to a binding partner of TYP1, such as a CDK. The second fusion protein comprises a transcriptional activation domain (e.g able to initiate RNA polymerase transcription) fused to the TYP1 polypeptide. When the CDK and TYP1 domains of each fusion protein interact, the two domains of the transcriptional activator protein are brought into sufficient proximity as to cause transcription of a reporter gene. By detecting the level of transcription of the reporter, the ability of a test agent to inhibit (or potentiate) the interaction can be evaluated. Commercial kits for generating interaction traps are presently available (e.g., MATCHMAKER Kit, Clontech catalog No. k1605-1, Palo Alto) and, in light of the present disclosure, can be modified for use as drug screening assays.

In an illustrative embodiment, *Sacchirduyces cerevisiae* YPB2 cells are transformed simultaneously with a plasmid encoding a GAL4db-CDK fusion and with a plasmid encoding the GAL4ad domain fused to a the Candida TYP1. Moreover, the strain is transformed such that the GAL4-responsive promoter drives expression of a phenotypic marker. For example, the ability to grow in the absene of histidine can depends on the expression of the HIS3 gene. When the HIS3 gene is placed under the control of a GAL4-responsive promoter, relief of this auxotrophic phenotype indicates that a functional GAL4 activator has been reconstituted through the interaction of the CDK and the TYP1 proteins. Thus, a test agent able to inhibit this interaction will result in yeast cells unable to growth in the absence of histidine. Alternatively, the phenotypic marker (e.g. instead of the HIS3 gene) can be one which provides a negative selection (e.g., are cytotoxic) when expressed such that agents which disrupt CDK/TYP1 interactions confer positive growth selection to the cells.

It will be apparent that, in similar fashion to the exemplary TYP1-derived assays, each of the other Candida regulatory proteins can be used to generate equivalent drug screening assays which provide a protein-protein interaction as the inhibitory target. For example, each of the CYB1, MOC1 and CKS1 proteins can be used to generate assays for detecting agents which inhibit interaction with a CDK, such as CDK1.

Moreover, for each of the subject regulatory proteins which have intrinsic enzymatic activities, such as the TYP1, CDK1, MOC1 and CMK1 proteins, the present invention provides methods and reagents for identifying agents which inhibit the enzymatic activity of the protein, e.g. agents which are mechanism based inhibitors of the enzyme, rather than merely disrupting the formation of a protein complex. Inhibitors of the enzymatic activity can be identified, for example, using assays generated for measuring the ability of an agent to inhibit catalytic conversion of a substrate by one of the subject enzymes. Again using TYP1 as an illustrative embodiment, a molecule or compound (e.g. a "test agent") to be assessed for its ability to inhibit the phosphatase activity of the subject TYP1 enzyme is combined with the enzyme and a substrate of its phosphatase activity. The resulting combination is maintained under conditions appropriate for the TYP1 enzyme to act upon the substrate. The conversion of the substrate to product by the subject TYP1 enzyme is assessed, and the result compared to the rate or level of conversion of the substrate in the absence of the test agent. A statistically significant decrease in the activity of the TYP1 phosphatase in the presence of the test agent, manifest as a decrease in conversion of substrate to product, indicates that the test agent is an inhibitor of the pathogen TYP1.

In preferred embodiments, the substrate of the TYP1 tyrosine phosphatase is a synthetic substrate, e.g. a peptide or tyrosine analog, comprising a colorimetric or fluorescent label which is detectable when the substrate is catalytically acted upon by the TYP1. As used herein "colorimetric" refers to substrates detectable by change in absorption or fluorescent characteristics. For instance, preferred synthetic substrates include p-nitrophenylphosphate (pNPP), fluorosceindiphosphate (FDP), 3-O-methylfluoroscein phosphate (3-MFP). Other chromogenic substrates include 3-(p-hydroxyphenyl) propionic acid (HPPA), 2-Naphthyl phosphate, pyridoxal phosphate, adamantyl 1,2-doxetance phosphate, disodium 3-(4-methoxyspirol {1,2-dioxetane-3, 2'-(5'-chloro) tricyclo [3.3.1.1] decan}-4-yl) phenyl phosphate, Thymolphtalein monophosphate, 3-indoxyl phosphate and the like. Yet other substrates include radiolabeled peptides, such as peptides containing $^{32}$P-labeled phosphotyrosines, e.g. tyrosine phosphorylated forms of reduced carboxamindomethylated, maleyated lyzosyme (RCML) or CDC-derived peptides, wherein release of the radiolabel can be detected and correlated with TYP1 enzymatic activity.

In an illustrative embodiment, the method comprises the steps of: (a) combining a compound to be assessed, the subject Candida TYP1 (purified or semipurified), and a synthetic substrate of the pathogen TYP1 tyrosine phosphatase comprising a calorimetric label which is detectable when the substrate is acted upon by the TYP1 (e.g., p-nitrophenylphosphate); (b) maintaining the substrate/enzyme/test compound combination under conditions appropriate for the pathogen-derived TYP1 to act upon the substrate; and (c) determining, by calorimetric assay, the extent to which the TYP1 enzyme present in the combination acted upon the substrate, relative to a control, the control comprising the TYP1 and the substrate. If the subject TYP1 enzyme acts upon the substrate to a lesser extent than in the control, the compound is an inhibitor of the pathogen TYP1 tyrosine phosphatase activity.

In yet another embodiment of the present invention, inhibitors of the subject regulatory proteins which are involved in positive growth regulations are identified through their ability to rescue an otherwise hyper-mitotic cell from mitotic catastrophe, e.g. such as described in U.S. patent application Ser. No. 08/073,383. The term hyper-mitotic cell denotes a cell having an impaired cell-cycle regulatory protein which can cause premature progression of the cell though at least a portion of the cell-cycle and ultimately resulting in cell death. The hyper-mitotic cell of the subject assay can be generated, for example, by disrupting expression of a gene whose product acts antagonistically to one of the subject proteins, by overexpressing one of the subject proteins, or a combination thereof. In preferred embodiments, the impaired checkpoint of the hyper-mitotic cell would, in normal cells, otherwise act as a negative regulator of downstream mitotic events induced by one of the regulatory proteins of the present invention. Impairment of such a negative regulator consequently allows the cell to proceed aberrantly toward subsequent mitotic stages and ultimately inhibits faithful proliferation of the cell. In the presence of an agent able to inhibit the function of the targeted regulatory protein, progression of the hyper-mitotic cell through the cell-cycle can be slowed to enable the cell to appropriately undergo mitosis and proliferate with fidelity.

The present assay therefore provides a simple and rapid screening test which relies on scoring for positive proliferation as indicative of agents able to inhibit the function of, for example, one of the Candida regulatory proteins of the present invention, e.g., TYP1, CDK1, CYB1 or MOC1. One advantage of the subject assay is that while direct inhibition of growth can be caused by any toxic compound added to a proliferating cell culture, growth stimulation in the present assay will only be achieved upon specific inhibition of the targeted regulatory protein. Another advantage of the present assay is the amenity of the assay to high through-put analysis.

With regard to the hyper-mitotic cell of the present assay, impairment of the regulatory protein can be generated so as to be either continual or conditional. A conditional impairment permits the checkpoint to be normatively operational under some conditions such that the cell may proliferate and be maintained by cell culture techniques; and be rendered inoperative, or alternatively hyper-operative, under other conditions. In the instance of the illustrative weel-50 mutant described below, the impaired checkpoint is effectively inoperative to an extent that the impairment allows aberrant mitosis to occur which concludes in mitotic catastrophe. A continual impairment, on the other hand, is one that is ever-present and which allows proliferation of the cell under conditions where there is no need to halt the cell at that checkpoint; but, in the instance of the hyper-mitotic cell, results in mitotic catastrophe under conditions where the cell-cycle must be halted, such as in the presence of DNA synthesis inhibitors or DNA damaging agents.

Regulatory pathways which feed into and modulate the activity of a CDK, such as CDK1, can be manipulated to generate the hyper-mitotic cell of the present assay. For example, as set out above, the inhibitory phosphorylation of cyclin-dependent kinases is mediated by at least two tyrosine kinases, initially identified in fission yeast and known as weel and mik1 (Russell et al. (1987) Cell 49:559; Lundgren et al. (1991) Cell 64:111; Featherstone et al. (1991) Nature 349:808; and Parker et al. (1991) EMBO 10:1255). These kinases act as mitotic inhibitors, overexpression of which causes cells to arrest in the G2 phase of the cell-cycle. For instance, overexpression of weel has been shown to cause intense phosphorylation of CDC2 (CDC28 in budding yeast) which results in cell-cycle arrest. Conversely, loss of function of weel causes advancement of mitosis and cells enter mitosis at approximately half the normal size, whereas loss of weel and mik1 function causes grossly premature initiation of mitosis, uncoupled from all checkpoints that normally restrain cell division. Thus, wee1 and mik1, or homologs thereof, each represent suitable regulatory proteins which could be impaired to generate the hyper-mitotic cell of the present assay.

Furthermore, it is apparent that enzymes which modulate the activity of the wee1 or mik1 kinases can also be pivotal in controlling the precise timing of mitosis. For example, the level of the nim1/cdr1 protein, a negative regulator of the wee1 protein kinase, can have a pronounced impact on the rate of mitotic initiation, and nim1 mutants have been shown to be defective in responding to nutritional deprivation (Russel et al. (1987) Cell 49:569; and Feilotter et al. (1991) Genetics 127:309). Over-expression of nim1 (such as the S. pombe op-nim1 mutant) can result in inhibition of the wee1 kinase and allow premature progression into mitosis. In like manner, mutation in the stfl gene has also been shown to relieve regulation of mitotic progression in response to DNA synthesis inhibition.

Loss-of-function strains, such as the S.Pombe weel-50, or miklmura (Rowley et al. (1992) Nature 356:353), are well known. In addition, each of the wee1, mik1, and nim1 genes have been cloned (see for example Coleman et al. (1993) Cell 72:919; and Feilotter et al. (1991) Genetics 127:309), such that disruption of wee1 and/or mik1 expression or over-expression of nim1 can be carried out to create the hyper-mitotic cell of the present assay. In a similar fashion, over-expression of wee1 and/or mik1 or disruption of nim1 expression can be utilized to generate a hypo-mitotic cell.

The hyper-mitotic cell of the present assay can be generated by manipulation of the cell in which one of the subject regulatory proteins expressed, as for example, by generating a wee1 mutation (a "wee" phenotype), or by exposure of the cell to 2-aminopurine or caffeine after a γ-radiation induced G2 arrest. It is also deemed to be within the scope of this invention that the hyper-mitotic cells of the present assay can be generated so as to comprise genetically engineered cells which express recombinant (e.g. heterologous) forms of the subject proteins. For instance, each of the subject recombinant TYP1, CDK1, MOC1 and CYB1 genes can be expressed in cells other than Candida, but in which the Candida gene is able to rescue lack-of-function mutations of the orthologous activity is the host cell. For example, the subject TYP1 gene can be used to replace the endogenous CDC25 gene of a hyper-mitotic Schizosaccharomyces cell, such as an S. pombe cell like the temperature-sensitive cdc25-22, wee1-50 mutant described below.

Moreover, in addition to complementation of CDC25-defective cells with the subject TYP1, the reagent cells of the subject assay can be further engineered to also express other exogenous cell-cycle proteins which interact with TYP1, e.g. Candida CDK. In an illustrative embodiment, a hyper-proliferative cell in which a Candida TYP1 is exogenously expressed can also be engineered to produce a Candida CDK (CDK1) and (optionally) a Candida cyclin (such as CYB1) and/or a CAK (e.g. MOC1). In this manner, the reagent cells of the present assay can be generated to more closely approximate the natural interactions which the pathogen phosphatase might experience.

In other embodiments, manipulation of cell-cycle regulatory pathways with certain drugs, termed here "hyper-mitotic agents", can induce mitotic aberrations and result in generation of the hyper-mitotic cell of the present assay. For instance, caffeine, the protein kinase inhibitors 2-aminopurine and 6-dimethylaminopurine, and the protein phosphatase inhibitor okadaic acid can cause cells that are arrested in S phase by DNA synthesis inhibitors to inappropriately enter mitosis (Schlegel et al. (1986) Science 232:1264; Schlegel et al. (1987) PNAS 84:9025; and Schlegel et al. (1990) Cell Growth Differ. 1: 171). Further, 2-aminopurine is believed to be able to override a number of cell-cycle checkpoints from G1, S phase, G2, or mitosis. (Andreassen et al. (1992) PNAS 89:2272; Andreassen et al. (1991) J Cell Sci. 100:299, and Steinmann et al. (1991) PNAS 88:6843). For example, 2-aminopurine permits cells to overcome a G2/M block induced by γ-irradiation. Additionally, cells continuously exposed to 2-aminopurine alone are able to exit S phase without completion of replication, and exit mitosis without metaphase, anaphase, or telophase events. The effect of inhibitors of, for example, TYP1 function can therefore act to slow the progression of the cell through the cell-cycle and, at appropriate concentrations, offset the effects of the hyper-mitotic agent so as to permit cell growth rather than mitotic catastrophe.

Furthermore, to aid in the facilitation of mitotic catastrophe in the hyper-mitotic cell it may be desirable to expose the cell to an agent (i.e., a chemical or environmental stimulus) which ordinarily induces cell-cycle arrest. Inappropriate exit from the chemically- or environmentally-induced arrested state due to the impairment of the negative regulatory checkpoint can ultimately be lethal to the cell. Such arresting agents can include exposure to DNA damaging radiation or DNA damaging agents; inhibition of DNA synthesis and repair using DNA polymerase inhibitors such as hydroxyurea or aphidicolin; topoisomerase inhibitors such as 4'-dimethly-epipodophyllotoxin (VM-26); or agents which interfere with microtubule-assembly, such as Nocadazole and taxol. By way of example, the weel-50 S. pombe cells described below can be dosed with γ-radiation in the presence of either caffeine, 2-aminopurine, or 6-dimethyl-aminopurine. Each of these compounds can suppress a G2 mitotic delay ordinarily caused by irradiation, and allow the cells to undergo mitosis before DNA repair has been completed. Inhibition of TYP1 activation of a CDK/cyclin complex may result in an offsetting effect which slows cell-cycle progression such that, at appropriate concentrations, the TYP1 inhibitor would rescue the hyper-mitotic cell. Additionally, in certain cells, nutritional status of the cell, as well as mating factors, can cause arrest of the normal cell during mitosis.

Agents to be tested for their ability to act as inhibitors can be produced by bacteria, yeast or other organisms (e.g. natural products), produced chemically (e.g. small molecules, such as peptidomimetics), or produced recombinantly. The assay can be carried out in any vessel suitable for the growth of the cell, such as microtitre plates or petri dishes. As potent inhibitors of the subject proteins would be expected to fully inhibit cell-cycle progression of even the hyper-mitotic cells, it will typically be desirable to perform the assay at various concentrations of the candidate agent. For example, serial dilutions of the candidate agents can be added to the hyper-mitotic cell such that at least one concentration tested the anti-mitotic agent inhibits the regulatory protein to an extent necessary to adequately slow the progression of the cell through the cell-cycle, but not to the extent necessary to completely inhibit entry of the cell into mitosis all together.

Quantification of proliferation of the hyper-mitotic cell in the presence and absence of a candidate agent can be measured using a number of techniques well known in the art, including simple measurement of population growth curves. For instance, where the assay involves proliferation in a liquid medium, turbidimetric techniques can be utilized (e.g., absorbence/transmittance of light of a given wavelength through the sample). For example, in the embodiment wherein the reagent cell is a yeast cell, measurement of absorbence of light at a wavelength between 540 and 600 nm can provide a conveniently fast measure of cell growth. Likewise, ability to form colonies in solid medium (e.g., agar) can be used to readily score for proliferation. Both of these techniques, especially with respect to yeast cells, are suitable for high through-put analysis necessary for rapid screening of large numbers of candidate agents. In addition, the use of solid media, such as agar-based plates, can further aid in establishing a serial dilution of the candidate agent. For example, the candidate agent can be spotted on a lawn of reagent cells plated on solid media. The diffusion of the candidate agent through the solid medium surrounding the site at which it was spotted will create a diffusional effect. For agents which inhibit the targeted regulatory protein, a halo of cell growth would be expected in an area which corresponds to concentrations of the agent which merely offset the effect of the impaired checkpoint, but which are not so great as to over-compensate for the impairment or too little so as to be unable to rescue the cell.

To further illustrate, other proliferative scoring techniques useful in the present assay include measuring the mitotic index for untreated and treated cells; uptake of detectable nucleotides, amino acids or dyes; as well as visual inspection of morphological details of the cell, such as chromatin structure or other features which would be distinguishable between cells advancing appropriately through mitosis and cells concluding in mitotic catastrophe or stuck at certain cell-cycle checkpoint.

EXEMPLIFICATION

The invention now being generally described, it will be more readily understood by reference to the following examples which are included merely for purposes of illustration of certain aspects and embodiments of the present invention, and are not intended to limit the invention.

As described herein, we have isolated and characterized several genes from Candida which encode proteins that regulate progress of the Candida cell through mitosis and/or meiosis. As described in example 1, a phosphatase, TYP1, was cloned from *C. albicans*, and determined to be related to the CDC25 phosphatase gene family. To validate the identity of the isolated gene, we demonstrate that it is able to rescue a temperature sensitive allele cdc25-22 of fission yeast. To salient features of the Candida TYP1 gene are: although the TYP1 gene has less than 50% homology with yeast cdc25 genes, and less than 10% homology with the human cdc25 genes, the enzyme apparently performs the same function in regulation of cell cycle progression. Furthermore, despite earlier reports that certain preparations of the cdc25 phosphatase would not hydrolyze synthetic substrates in vitro (see Gautier et al. (1991) *Cell* 67:197–211, recombinant forms (including bacterially expressed) of the Candida TYP1 enzyme are able to hydrolyze such substrates.

EXAMPLE 1

Cloning of Candida TYP1

In order to isolate a gene encoding a Candida TYP1 phosphatase, the degenerate oligonucleotides ATGGATC-CYTTRTANCCNCCRTSNARNANR-TANAYNTCNGGRTA (SEQ ID No. 13), ATGGATCCATI-ATIGAYTGYMGITWYCCITAYGA (SEQ ID No. 14), and ATGGATCCATIATIGAYTGYMGITWYGAITAYGA (SEQ ID No. 15) were used to amplify *C. albicans* genomic DNA in λZAP (strain 3153A) by standard PCR protocols. The PCR reaction products were separated on a 2.5% low melting agarose gel that identified a sizable fragment (approximately 250 BP). The fragment was cloned into the pCRII vector (TA cloning system, *Invitrogen*) and the nucleotide sequence confirmed the identity of the insert as a likely TYP1 phosphatase. DNA probes were generated as $^{32}$P-labeled nick translation products of the fragment, and used to further screen *C. albicans* cDNA libraries. Larger cDNA clones were isolated by this technique, and sequenced. The sequence of the open reading frame of the Candida TYP1 gene is given in SEQ.ID. No. 1, which also includes both 5' and 3' non-coding sequences.

To validate the identity of the isolated cDNA, the TYP1 clone was tested for its ability to rescue the temperature sensitive allele cdc25-22 of the fission yeast. Briefly, a 1.2 kbp EcoRI insert containing most of the open reading frame but lacking the amino part was cloned into the SmaI site of the pART1 vector, the resulting vector being designated pART-TYP1. As described in the literature, e.g. see WO 94/28914 , the pART1 vector contains the constitutive *S. pombe* ADH promoter, the arsI fragment for replification and the *S. cerevisiae* LEU2 gene as a marker which complements the leu1-32 mutant in *S. pombe*. Transformants growing on medium lacking leucine were streaked on plates and transferred at permissive temperature (37° C.). It was observed that only the cells expressing the *C. albicans* gene were able to form colonies. Microscopic observations of the cells revealed the rescue from the cell elongation typical for this mutant at restrictive temperature.

Figure 1B:
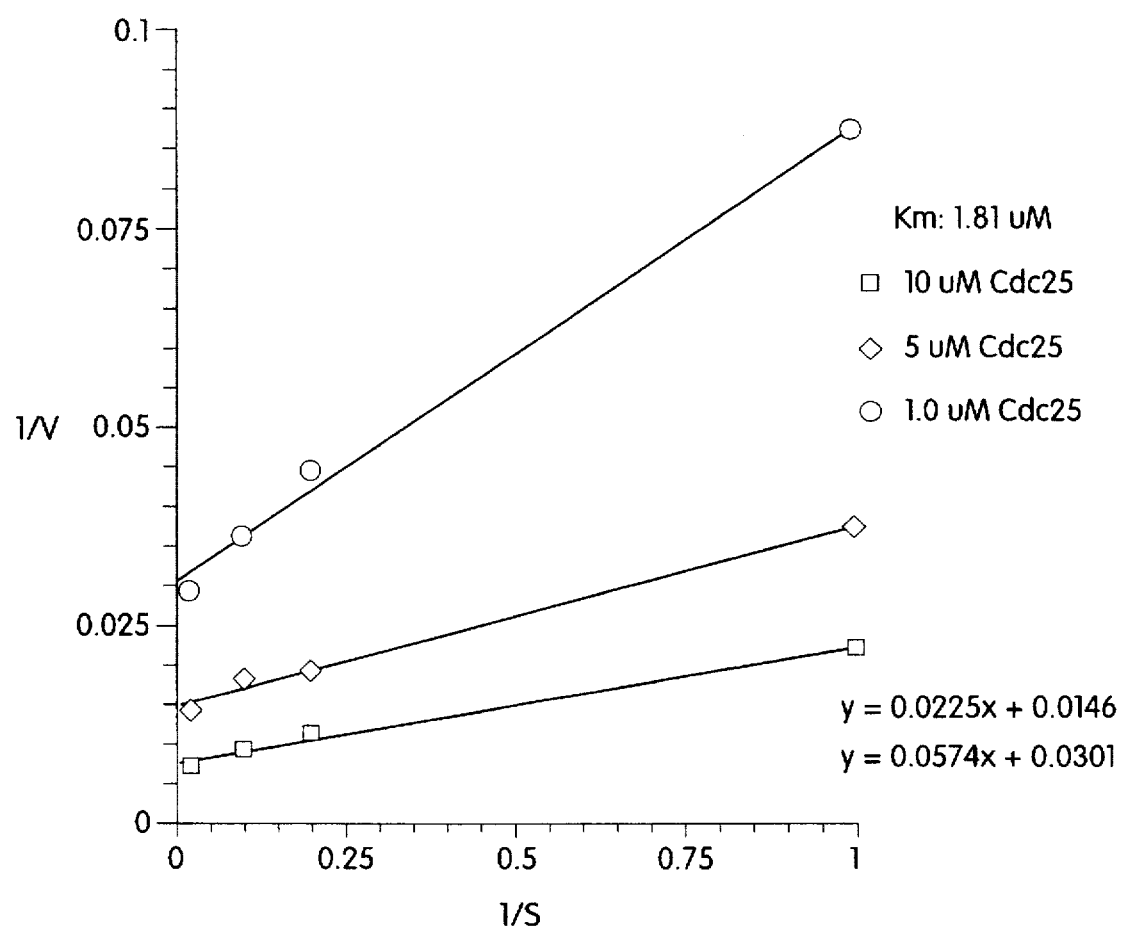
FIG. 1B demonstrates a Lineweaver-Burke analysis for recombinant Candida TYP1 hydrolysis of fluoroscein diphosphate.

The *C. albicans* TYP1 cDNA gene was subsequently used to derive a fusion protein with glutathione-s-transferase in bacterial cells. Briefly, the EcoRI fragment described above was cloned into the EcoRI site of pGEX-4T-1 (Pharmacia). Expression of the fusion protein in *E. coli* was induced by addition of IPTG (1 mM) to the culture medium. After 4 hours of this regimen, cells were pelleted and resuspended in PBS plus various protease inhibitors. The cell suspension was then sonicated and centrifuged to pellet the cell debris. The soluble fraction was collected and analyzed on SDS-PAGE and tested for phosphatase activity. The expression of the fusion protein was confirmed by Western Blot using an anti-GST antibody. As demonstrated in FIGS. 1A and 1B, the recombinant Candida TYP1 phosphatase was active against both para-nitrophenylphospate and fluoroscein diphosphate.

EXAMPLE 2

Cloning of *Candida albicans* CKS1

In similar fashion to the cloning of the Candida TYP1 gene, a suc1 homolog was cloned from a Candida genomic library by PCR amplification using the primers TWYGAR-TAYMGNCAYGTNATG (SEQ ID No. 16) and AANAR-NARDATRTGNGGYTC (SEQ ID. No. 17). As above, the PCR fractions were separated on an agarose gel, the fragment eluted, and cloned into pCRII. DNA probes were generated as $^{32}$P-labeled nick translation products, and used to further screen a *C. albicans* cDNA library. Larger CDNA clones isolated by this technique were sequenced. The nucleotide sequence for the CKS1 open reading frame, plus flanking noncoding sequence, is provided in SEQ. ID. No. 2.

The CKS1 coding sequence was subcloned into a pQE vector (Qiagen), and used to produce native proteins. The purified proteins should isolate the Candida CDK1 from cell lysates.

EXAMPLE 3

Cloning of a Candida cyclin-dependent kinase

Using the degenerate oligonucleotides TCNGGNGC-NCKRTACCANARNGT (SEQ ID No. 18) and GGN-GARGGNACNTAYGGNGTNGT (SEQ ID No. 19), a cyclin-dependent kinase was isolated from a C. albicans genomic library by PCR. The amplification program consisted of 30 cycles: 94° C. for 1 min., 50° C. for 1 min., and 72° C. for 1 min. Two major PCR reaction products were generated, separated on an agarose gel, and subsequently cloned into the pCRII vector, followed by standard Sanger sequencing. One of the two clones, a 490bp fragment, exhibited a reasonable degree of similarity with other members of the CDK gene product family and was accordingly used to screen a C. albicans cDNA library.

Purified probes were generated as $^{32}$P-labeled nick translation products, and hybridization was performed at 53° C. overnight in Church's solution (7% SDS, 250mM NaP pH 7's, 10, mM, EDTA, pH7) and filters were washed twice at the same temperature in a buffer obtaining 2×SSC and 0.1% SDS. The open reading frame for the cyclin-dependent kinase, referred to herein as CDK1, is given in SEQ. ID. No. 3.

EXAMPLE 4

Cloning of a C. albicans cyclin

As above, the degenerate primers GANGANYKNGMN-GANCCNYTNATG (SEQ ID No. 20) and ATNCKNCK-NARRAARTTCAT (SEQ ID No. 21) were used to amplify C. albicans genomic DNA. The amplification program consisted of 30 cycles: 94° C for 1 minute, 43° C. for 1 minute, and 72° C. for 1 minute. Two reaction products of about 450 and 700 bp were separated on an agarose gel. The 450 bp DNA fragment was reamplified and cloned into the pCRII vector and then used to screen a C. albicans cDNA library. An apparent cyclin B homolog, referred to herein as CYB1, was isolated from the CDNA library. The open reading frame for this cyclin is given by SEQ. ID. No. 4.

In C. albicans and C. maltosa, the CUG codon, which encodes leucine in the universal codon usage, is believed to be translated as serine (amino acid residues 301 and 383 of SEQ ID NO. 4). See, for example, Sugiyama et al. (1995) Yeast 11:43–52 and Zimmer et al. (1995) Yeast 11:33–41. Accordingly, it will be understood that an equivalent gene for expression in other cells can be modified at these positions to a codon for serine. However, it is noted that expression of the CYB1 gene in S. pombe produced what is apparently a functional protein, suggesting that these residues do not effect the biological activity of the cyclin, or that Sugiyama et al. were incorrect.

Sequence CLUSTAL alignment method (Higgins et al. (1992) Comp. Appl. Bio-Sci. 8:189–191) was run on the MegAlign program in the DNAStar package showed that the C. albicans CYB1 gene product is 34.8%, 34.4%, 35.5.%, 33.3%, and 33.7% identical to the S. cerevisiae Clb1, Clb2 (Fitch et al. (1992) Mol. Biol. Cell 3:805–818), S. pombe Cdc13 (Booher et al.(1988) EMBO J. 7:2321–2327; Hagan et al. (1988) J. Cell Sci. 91:587–595), Cig2 (Connolly et al. (1994) Mol. Cell. Biol 14:768–776) and A. nidulans NimE (O'Connell et al. (1992) EMBO J. 11:2130–2149) proteins, respectively. Percentages of identity increase up to 57% when only the C-terminal parts, containing the cyclin box, of the fungi B-type cyclins are aligned. The destruction box (RQYLGDVSN, amino acids 67 to 75 of CYB1) matches perfectly the consensus RxxLxxxxN which is essential for cyclin degradation via the ubuquitin pathway (Glotzer et al. (1991) Nature 349:132–138). The P box, which is required for Cdc25 activation by the MPF complex (Galaktionov et al. (1991) Cell 67:1181–1194; Zheng et al. (1993) Cell 75:155–164) is also present on the C. albicans Cyb1 protein (amino acids 237 to 268, SEQ ID NO. 4). Cyb1 P box is 58.8%, 64.7%, 67.6%, 61.8% and 70.6% identical to the S. cerevisiae Clb1, Clb2, S. pombe Cdc13, Cig2, and A. nidulans NimE P boxes, respectively.

EXAMPLE 5

C albicans CDK1 Complements the S. pombe cdc2-33 Temperature Sensitive Mutation To test if the CDK1 cDNA is a functional gene the full length CDK1 cDNA was cloned into the S. pombe pART1 expression vector (McLeod et al. (1987) EMBO J. 6:729–736), yielding pCDK1.5. pART1 contains the S. cerevisiae LEU2 gene that complements a S. pombe leu1-32 mutation, the S. pombe ars1 sequence, and the S. pombe adh promoter which initiates strong and constitutive transcription. pCDK1.5 was used to transform the temperature sensitive S. pombe cdc2-33 strain (Nurse et al. (1976) Nature 146:167–178). Transformants were obtained at 25° C., which is the permissive temperature for cdc2-33. They were then streaked for single colonies and incubated at 25° C., 35° C, or 37° C. The C. albicans CDK1 gene enables a S. pombe cdc2-33 strain to form colonies at both 35° C. and 37° C., however, complementation is not as good as when the S. pombe wild-type cdc2 gene is used.

EXAMPLE 6

C. albicans CYB1 Complements the S. pombe cdc12-117 Temperature Sensitive Mutation To test if the CYB1 cDNA is a functional gene the full length CYB1 cDNA was cloned into the S. pombe pART1 expression vector (Mc Leod et al. (1987) EMBO J. 6:729–736). The resulting plasmid pCYB1.5 was used to transform a temperature sensitive S. pombe cdc13-117 strain (Nasmyth et al. (1981) Mol. Gen. Genet. 182:119–124). Transformants obtained at 25° C. were then streaked for single colonies and incubated at 25° C., 35° C., or 37° C. The C. albicans CYB1 gene product is able to rescue a S pombe cdc13-117 mutation at 35° C., but no colony formation was observed at 37° C, indicating a partial rescue.

EXAMPLE 7

Interaction Between the CDK1 and CYB1 Proteins

Using the primers GACCAACACGAATTCCAAATGG-TAGAGTTATCTG (SEQ ID No. 22) and TGAGGAGTC-GACCAAGATTTATTGCATG (SEQ ID No. 23), which contain EcoRI and a SalI restriction sites, respectively, the CDK1 coding sequence was amplified and subcloned into pEG202 vector in order to created a CDK1-LexA fusion protein. Likewise, the CYB1 coding sequence was amplified with the oligonucleotides CATTTTGAATTCATAGTAAT-GCCACAAGTC (SEQ ID No. 24) and ATAGTCCTC-GAGACTTTACTCTTCTGCTTC (SEQ ID No. 25), cut with EcoRI and XhoI, and the restriction fragment was subcloned into the vector pJG4-5 (Gyuris et al. (1993) Cell 75:791–803) in order to generate a CYB1-VP16 fusion protein.

The two vectors were used to simultaneously transform the S. cerevisiae strain YEG048 so as to constitute an interaction trap assay. Analysis of the transformants revealed that the CDK1 and CYB1 proteins interact with one another.

EXAMPLE 8

Generation of a TYP1-Dependent Hypermitotic Cell

When the TYP1 plasmid construct pART-TYP1, described above, is used to transform the *S. Pombe* strain Sp553 (h+N, cdc25-22, weel-50, leu1-32) using well known procedures. Briefly, cells are grown in YE medium at 25° C. until they were in exponential phase ($10^7$ cells/ml). The cells are then spun down from the media at 3000rpm for 5 minutes, and resuspended in LiCl/TE at a concentration of ~$10^8$ cells/ml (LiCl/TE=10 mM Tris, 1 mM EDTA, 50 mM LiCl, pH 8). The resuspended cells are incubated at room temperature for 10 minutes, then spun again at 3000 rpm for 5 minutes, resuspended in LiCl/TE to a concentration of ~$5 \times 10^8$ cells/ml, and shaken for 30 minutes at 25° C.

To an aliquot of 150 µl of cells, 500 ng of plasmid DNA and 350 µL of PEG/TE (10 mM Tris, 1 mM EDTA, 50% PEG 4000, pH 8) is added. The cell/plasmid mixture is then incubated for 30 minutes at 25° C., heat shocked at 42° C. for 20 minutes, then spun at 15,000 rpm for 10 seconds after the addition of 0.5 mL of Edinburgh Minimal Medium (EMM). The cells were resuspended in 0.6 mL EMM, and 0.2 mL aliquots were plated.

At the non-permissive temperature of 37° C., both the endogenous weel and CDC25 activities of the Sp553 cells are impaired such that they mutually off-set each other's effects, and the cells are still able to proliferate. However, the effect of expressing the recombinant Candida TYP1 protein in a yeast "wee" background results in mitotic catastrophe. For example, at the permissive temperature of 25° C. (weel is expressed) the cells are able to proliferate. However, shifting the temperature to the non-permissive temperature of 37° C results in mitotic catastrophe.

EXAMPLE 9

Assay for TYP1 Inhibitors Using a Hypermitotic Cell

To assay the anti-mitotic activity of various candidate agents, the cells of Example 6 are either plated on a solid medium such as EMM plates or suspended in an appropriate vegetative broth such as YE.

In the instance of plating on a solid medium, candidate agents are subsequently blotted onto the plate, and the plate incubated at the non-permissive temperature of 37° C. A halo of cell growth will form surrounding those agents able to at least partially inhibit a mitotic activator which can rescue the otherwise catastrophic cell.

Where growth of the cells is carried out in a vegetative broth, aliquots of cell/media are placed in the wells of microtitre plates and serial dilutions of candidate agents are added to the wells. The plates are incubated at 37° C., and the $A_{595}$ for each well measured over time and compared to similar wells of cells/media which lack the candidate agent (e.g. negative controls). An increase in absorbence over time relative to the negative controls indicates positive proliferation of the cells and suggests an ability of a particular candidate agent to inhibit a mitotic activator.

All of the above-cited references and publications are hereby incorporated by reference.

EQUIVALENTS

Those skilled in the art will recognize, or be able to ascertain using no more than routine experimentation, numerous equivalents to the specific assay and reagents described herein. Such equivalents are considered to be within the scope of this invention and are covered by the following claims.

---

We claim:

1. A substantially pure nucleic acid comprisng a TYP1 nucleotide sequence which encodes a TYP1 polypetide which polypeptide includes a catalytic domain and catalyzes dephosphorylation of a cyclin-dependexnt kinase. (cdk), wherein the TYP1 nucleotide sequence hybridizes under high stringency conditions to the TYP1 coding sequence of SEQ ID No. 1.

2. An isolated nucleic acid comprising a TYP1 nucleotide sequence which encodes a TYP1 polypeptide, wherein: (i) the TYP1 nucleotide sequence hybridizes under high stringency conditions to the TYP1 coding sequence of SEQ ID No. 1; and (ii) the TYP1 polypeptide has an amino acid sequence of a naturally occurring TYP1 protein of a Candida organism, and includes a catalytic domain which catalyzes dephosphorylation of a cyclin dependent kinase (cdk).

3. The nucleic acid of claim 1 or 2, wherein the TYP1 polypeptide activates a Candida cyclin dependent kinase.

4. The nucleic acid of claim 1 or 2, wherein the TYP1 polypeptide hydrolyzes p-nitrophenylphosphate, fluorosceindiphosphate, or 3-O-methylfluoroscein phosphate.

5. The nucleic acid of claim 1 or 2, which TYP1 nucleic acid further comprises a transcriptional regulatory sequence operably linked to said nucleotide sequence so as to render said nucleotide sequence suitable for use as an expression vector.

6. The nucleic acid of claim 1 or 2, wherein the TYP1 polypeptide is a fusion protein.

7. The nucleic acid of claim 6, wherein the fusion protein is a glutathione-S-transferase (GST) fusion protein.

8. The nucleic acid of claim 1 or 2, wherein the TYP1 polypeptide corresponds in size to the full-length TYP1 protein of SEQ ID No. 7.

9. The nucleic acid of claim 1 or 2, wherein the TYP1 nucleotide sequence hybridizes under high stringency conditions to at least 120 consecutive nucleotides of the TYP1 coding sequence of SEQ ID No. 1.

10. The nucleic acid of claim 1 or 2, wherein the TYP1 polypeptide rescues a temperature sensitive cdc25-22 *Schizosaccharomyces pombe* cell.

11. The nucleic acid of claim 1 or 2, wherein the TYP1 polypeptide has an amino acid sequence of a naturally occurring TYP1 protein of a Candida organism.

12. A substantially pure nucleic acid comprising a TYP1 nucleotide sequence, encoding the TYP1 polypeptide of SEQ ID No. 2, which TYP1 polypeptide includes a catalytic domain which catalyzes dephostborylation of a cyclin dependent kinase (cdk).

13. A substantially pure nucleic acid comnprising a TYYP1 nuclotide snquence whiqh encodes a TVP polpeptide wherein the TYP1 nucleotide sequence is identical to the TYP1 coding sequence of SEQ ID No. 1.

14. An expression vector, capable of replicating in at least one of a prokaryotic cell and eukaryotic cell, comprising the nucleic acid of claim 1 or 2.

15. A host cell culture transfected with the expression vector of claim 14.

16. The host cell of claim 15, wherein the host cell is a Schizosaccharomyces cell.

17. The host cell of claim 16, wherein the host cell is a *Schizosaccharomyces pombe* cell.

18. The host cell of claim 16, wherein the host cell has a conditionally impairable weel protein kinase which can cause cell death by facilitating premature entry of the cell into mitosis under conditions wherein the weel protein kinase is impaired, the premature entry into mitosis being mediated at least in part by expression of the TYP1 polypeptide.

19. The host cell of claim 18, wherein the weel protein kinase is temperature sensitive and is impaired at a temperature above a permissive temperature.

20. A method of producing a recombinant Candida TYP1 polypeptide comprising culturing the cell of claim 15 in a cell culture medium to express said TYP1 polypeptide, and isolating said TYP1 polypeptide from said cell culture.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 1668 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 259..1491

( x i ) SEQUENCE DESCRIPTION: SEQ ID NO:1:

```
GGATGATACA  AATGTGGAAG  ATGCAAATTG  TTCTTCCCCT  ACTTTGATGA  GAAAAAGTGC      60

ATTGAGTAAA  ATCATCTTCA  AAGGACATTA  AACAATAATT  CCAAATCACC  ATCGCCAACT     120

TTTTCAAATA  CAAATGCAAC  ATCTGGCTCT  CCATTGTCAA  ATCTTTCTCG  TGCACCATTG     180

AGAAATTTAT  CTAATTTCGT  TATTCCTTCG  TCAGTTAAAT  CAAAAACGAA  ACAATTTACA     240
```

```
AACTCTTTGA CTCGTTCA ATG ACT GAA GTG GTT TCG AAA TCA TCA CAC TCA                    291
                     Met Thr Glu Val Val Ser Lys Ser Ser His Ser
                      1           5                      10

TTT TTC AAT AAT TTG CAT CTT GCA ACC TCA ACT GCG TCT TCT TCA GTA                    339
Phe Phe Asn Asn Leu His Leu Ala Thr Ser Thr Ala Ser Ser Ser Val
            15                  20                  25

TCG AGC ACA ACT CCC AAA ATA GAA TTC AAT TCC ATA GCT GAA AAT GAT                    387
Ser Ser Thr Thr Pro Lys Ile Glu Phe Asn Ser Ile Ala Glu Asn Asp
                30              35              40

GAT ATC CCT ACC AAT TAT GAC TCT GAT GAA GAA TTC GAA GAT GGT GAT                    435
Asp Ile Pro Thr Asn Tyr Asp Ser Asp Glu Glu Phe Glu Asp Gly Asp
        45                  50                  55

ACG TTT ATA CAA TCC ACC TTG ATT CAC CAG TTC AAC GCA AGT CAA GTA                    483
Thr Phe Ile Gln Ser Thr Leu Ile His Gln Phe Asn Ala Ser Gln Val
60                  65                  70                  75

ACA ACA ACA ACA ATA ATA ATA ATA CCA ATG ATG GTA ACG ACA ATA ATA                    531
Thr Thr Thr Thr Ile Ile Ile Ile Pro Met Met Val Thr Thr Ile Ile
                    80              85                  90

TAC CTA CAA AAA TTA GAC GGT TCC ACT CCA TGT ACC AAA CCG ATA AAG                    579
Tyr Leu Gln Lys Leu Asp Gly Ser Thr Pro Cys Thr Lys Pro Ile Lys
                95              100             105

AGA TTG CAT CGT ACC AAC TTC ATG AAG ATA ATT CAT TTT GAA ATT TAC                    627
Arg Leu His Arg Thr Asn Phe Met Lys Ile Ile His Phe Glu Ile Tyr
        110                 115                 120

AAT ATT GAA TAT TCT CAT CTG GAG AGT GAT TTG TTA CCA CGA ATC GAT                    675
Asn Ile Glu Tyr Ser His Ser Glu Ser Asp Leu Leu Pro Arg Ile Asp
125                 130                 135

GCT CAT CAA TTA GCC AGA ATA TTA CGT GGA GAC CAC GAT GAC CAA TTT                    723
Ala His Gln Leu Ala Arg Ile Leu Arg Gly Asp His Asp Asp Gln Phe
140                 145                 150                 155

GAT GAA TTT ATT ATC ATT GAT TGT CGA TTT GAG TAT GAA TTT AAT GGT                    771
Asp Glu Phe Ile Ile Ile Asp Cys Arg Phe Glu Tyr Glu Phe Asn Gly
                160                 165                 170

GGC CAT ATT ACT AGG GCA ATC AAT ATC TCC ACC CAG GAA GCA CTT CAA                    819
Gly His Ile Thr Arg Ala Ile Asn Ile Ser Thr Gln Glu Ala Leu Gln
            175                 180                 185

GAA AAG CTC TTT CAA TAT CAA GAA ACA GAT ACC AAG GAC ACT GAA AGC                    867
Glu Lys Leu Phe Gln Tyr Gln Glu Thr Asp Thr Lys Asp Thr Glu Ser
        190                 195                 200

AAG AAG CGA TTG ATA ATT TTC CAT TGT GAG TTC AGT ATG TTC AGA GGA                    915
Lys Lys Arg Leu Ile Ile Phe His Cys Glu Phe Ser Met Phe Arg Gly
205                 210                 215

CCA ATG ATG GCC AAA CAT TTA AGA AAG TGT GAT AGA ATG TGC AAC TAC                    963
Pro Met Met Ala Lys His Leu Arg Lys Cys Asp Arg Met Cys Asn Tyr
220                 225                 230                 235

GAC AAT TAT CCT CTA TTA ACA TAC CCC GAT ATT GCA ATT TTG GAA GGA                   1011
Asp Asn Tyr Pro Leu Leu Thr Tyr Pro Asp Ile Ala Ile Leu Glu Gly
                240                 245                 250

GGC TAT AAG AAT TTC TAT GAA AAT TAC CCC CAA TGG TGT GAT CCT CAA                   1059
Gly Tyr Lys Asn Phe Tyr Glu Asn Tyr Pro Gln Trp Cys Asp Pro Gln
            255                 260                 265

GGA TAT GTC GAG ATG AAG AAT TTA CGA CAC AAA AAA TTA TGT GAA TCC                   1107
Gly Tyr Val Glu Met Lys Asn Leu Arg His Lys Lys Leu Cys Glu Ser
        270                 275                 280

AAC TTG GAT AAA GTT AGA AAA GAT AAT AAA CTA ACT AGA GCA AAG TCT                   1155
Asn Leu Asp Lys Val Arg Lys Asp Asn Lys Leu Thr Arg Ala Lys Ser
285                 290                 295

TAT CAA TTT GGT ATT CAA CAC CGC CGT GGT GGT TCC ACT GGT GGA CTT                   1203
Tyr Gln Phe Gly Ile Gln His Arg Arg Gly Gly Ser Thr Gly Gly Leu
300                 305                 310                 315
```

| | | | | | | | | | | | | | | | | |
|---|---|---|---|---|---|---|---|---|---|---|---|---|---|---|---|---|
| TTC | GGC | AAC | TAT | AAT | TAC | AAC | GTT | ATG | AAC | TCA | TCA | GAT | CAA | CAA | TTT | 1251 |
| Phe | Gly | Asn | Tyr | Asn 320 | Tyr | Asn | Val | Met | Asn 325 | Ser | Ser | Asp | Gln | Gln 330 | Phe | |
| TGG | AGT | AGC | AGT | ACT | TCC | AAC | ACT | GCT | CAC | CAC | AGA | AGT | AGT | AGC | AGT | 1299 |
| Trp | Ser | Ser | Ser 335 | Thr | Ser | Asn | Thr | Ala 340 | His | His | Arg | Ser | Ser 345 | Ser | Ser | |
| AGC | GGG | TTC | ATT | AAT | AAT | ATG | CAT | AGT | GGT | GCT | TCG | TCA | TAT | CAC | CAT | 1347 |
| Ser | Gly | Phe 350 | Ile | Asn | Asn | Met | His 355 | Ser | Gly | Ala | Ser | Ser 360 | Tyr | His | His | |
| AGG | TCA | CAA | TCG | TTT | GTA | ACT | ATC | AAT | AAT | GAG | AAA | ATT | ATC | AAG | CGA | 1395 |
| Arg | Ser 365 | Gln | Ser | Phe | Val | Thr 370 | Ile | Asn | Asn | Glu | Lys 375 | Ile | Ile | Lys | Arg | |
| CAA | AGA | TCG | ACT | CCC | AAA | GTC | AGC | AAC | TCA | CCA | ACC | AAG | CCA | CCT | CAT | 1443 |
| Gln 380 | Arg | Ser | Thr | Pro | Lys 385 | Val | Ser | Asn | Ser | Pro 390 | Thr | Lys | Pro | Pro 395 | His | |
| CAA | CTG | TAT | CTC | CTG | ATA | AAC | CCA | TTC | CGT | TGG | CTA | ATA | TTC | ATA | GAT | 1491 |
| Gln | Ser | Tyr | Leu | Ser 400 | Ile | Asn | Pro | Phe | Arg 405 | Trp | Leu | Ile | Phe | Ile 410 | Asp | |
| TAACTCGTGC | CAACACTATT | TCATCAGACC | AAACATTGTT | TAGCAATAAG | CTGGTATCTT | | | | | | | | | | | 1551 |
| CCCCAATGAT | ATCTCCACTT | GCAGCTAGTT | TTGAACAATC | GTCGATTGGA | ATAAGTTCTT | | | | | | | | | | | 1611 |
| CTGAATTATC | AGTCAATACT | CAAGATTTTC | AACCACCGAC | TACGTCCTTT | AGGAATT | | | | | | | | | | | 1668 |

( 2 ) INFORMATION FOR SEQ ID NO:2:

( i ) SEQUENCE CHARACTERISTICS:
        ( A ) LENGTH: 786 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 208..513

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| AACTTGTTTA | CTTATTTGTT | TATATAATTG | ATAGATATCA | ATTACTAATT | TACCCTTGTT | | | | | | | | | | | 60 |
| TTTTACTTCC | TACTATTCAA | GACTTTATTT | CCTCCTGATA | ATCATTTTGT | TTGATTATCA | | | | | | | | | | | 120 |
| TTTTCGTCAA | TTAGTTCTTT | TTTTTCATTT | GTTCCAGAG | TTTAGGAAGA | CTACCATTTT | | | | | | | | | | | 180 |
| ACAATTTTCA | ATTCAAATAT | TTCCCA | ATG | ACT | AAA | CCA | AGA | TTT | TTA | ACA | | | | | | 231 |
| | | | Met 1 | Thr | Lys | Pro | Arg 5 | Phe | Leu | Thr | | | | | | |
| AGA | TAT | AGA | AAG | AGC | AAA | AGT | GTT | GGA | ATT | TCA | GAT | ATG | ATC | CAT | TAC | 279 |
| Arg | Tyr 10 | Arg | Lys | Ser | Lys 15 | Ser | Val | Gly | Ile | Ser 20 | Asp | Met | Ile | His | Tyr | |
| AGT | CCC | AGA | TAC | AGT | GAT | GAT | TCA | TAC | GAG | TAT | AGA | CAT | GTG | ATG | TTA | 327 |
| Ser 25 | Pro | Arg | Tyr | Ser 30 | Asp | Asp | Ser | Tyr | Glu 35 | Tyr | Arg | His | Val | Met 40 | Leu | |
| CCC | AAG | AAT | ATG | TTG | AAA | GCA | ATT | CCT | CAC | GAT | TAC | TTT | AAT | CAA | GAA | 375 |
| Pro | Lys | Asn | Met | Leu 45 | Lys | Ala | Ile | Pro | His 50 | Asp | Tyr | Phe | Asn | Gln 55 | Glu | |
| ACA | GGT | ACT | TTG | AGG | ATA | TTG | ACA | GAA | GAA | GAA | TGG | AGA | GGG | TTA | GGA | 423 |
| Thr | Gly | Thr | Leu 60 | Arg | Ile | Leu | Thr | Glu 65 | Glu | Glu | Trp | Arg | Gly 70 | Leu | Gly | |
| ATC | ACA | CAA | TCT | TTG | GGT | TGG | GCC | CAT | TAC | GAA | ACT | CAT | GCT | CCA | GAG | 471 |
| Ile | Thr | Gln 75 | Ser | Leu | Gly | Trp | Ala 80 | His | Tyr | Glu | Thr | His 85 | Ala | Pro | Glu | |
| CCT | CAT | ATA | TTA | TTA | TTC | AAG | AGA | CCC | TTA | AAT | CCC | GGG | CAA | | | 513 |
| Pro | His | Ile 90 | Leu | Leu | Phe | Lys | Arg 95 | Pro | Leu | Asn | Pro | Gly 100 | Gln | | | |

39

-continued

| TAAAAAGATT | AACTATATTT | GAATACTATA | GAATCGGAAT | CGGTTTTAAA | GTTAACACTG | 573 |
| GAATTAAAAC | ATAAAAGGA | AAGAAATAGC | CCATTGGTCA | CAGTAATCTG | TTTCCAACAA | 633 |
| CCCCCCTCCT | CAGAAATAGG | ATAGAAATGA | ATTAACGATG | AATTTGTATA | CACTATTTAT | 693 |
| AAGCCAATCT | CATTGATTGC | ATTTCTTATT | TGTATATTAT | TAAATACGTA | TATCGCGAGA | 753 |
| AACTGTATAA | ATACTCTTGG | TACCTCGCAT | GTT | | | 786 |

( 2 ) INFORMATION FOR SEQ ID NO:3:

( i ) SEQUENCE CHARACTERISTICS:
        ( A ) LENGTH: 1002 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 43..993

( x i ) SEQUENCE DESCRIPTION: SEQ ID NO:3:

```
TAGAACACAC ACATCCCAAG CCAAGACCAA CACTTATTGC AA ATG GTA GAG TTA          54
                                                Met Val Glu Leu
                                                 1

TCT GAT TAT CAA CGT CAA GAA AAA GTC GGA GAA GGT ACT TAT GGG GTT        102
Ser Asp Tyr Gln Arg Gln Glu Lys Val Gly Glu Gly Thr Tyr Gly Val
  5              10                  15                  20

GTT TAT AAA GCA TTA GAT ACC AAG CAC AAT AAT AGA GTT GTT GCA TTA        150
Val Tyr Lys Ala Leu Asp Thr Lys His Asn Asn Arg Val Val Ala Leu
             25                  30                  35

AAG AAA ATT CGA TTA GAA TCA GAA GAT GAA GGT GTA CCT AGT ACC GCC        198
Lys Lys Ile Arg Leu Glu Ser Glu Asp Glu Gly Val Pro Ser Thr Ala
         40                  45                  50

ATT AGA GAA ATC TCG TTA TTA AAA GAA ATG AAA GAT GAT AAT ATC GTT        246
Ile Arg Glu Ile Ser Leu Leu Lys Glu Met Lys Asp Asp Asn Ile Val
     55                  60                  65

CGA TTA TAT GAT ATT ATT CAT TCA GAT TCT CAT AAA TTA TAT TTA GTA        294
Arg Leu Tyr Asp Ile Ile His Ser Asp Ser His Lys Leu Tyr Leu Val
 70                  75                  80

TTT GAA TTT TTG GAT TTA GAT TTA AAG AAA TAT ATG GAA AGT ATT CCT        342
Phe Glu Phe Leu Asp Leu Asp Leu Lys Lys Tyr Met Glu Ser Ile Pro
 85                  90                  95                 100

CAA GGA GTT GGA CTA GGG GCT AAT ATG ATA AAA AGA TTT ATG AAT CAA        390
Gln Gly Val Gly Leu Gly Ala Asn Met Ile Lys Arg Phe Met Asn Gln
                105                 110                 115

TTA ATT CGA GGT ATT AAA CAT TGT CAT TCT CAT CGA GTT TTA CAT CGT        438
Leu Ile Arg Gly Ile Lys His Cys His Ser His Arg Val Leu His Arg
            120                 125                 130

GAT TTA AAA CCA CAA AAT TTA TTG ATT GAT AAA GAA GGG AAT TTA AAA        486
Asp Leu Lys Pro Gln Asn Leu Leu Ile Asp Lys Glu Gly Asn Leu Lys
        135                 140                 145

TTA GCA GAT TTT GGA TTA GCT CGA GCA TTT GGA GTT CCA TTA AGA GCA        534
Leu Ala Asp Phe Gly Leu Ala Arg Ala Phe Gly Val Pro Leu Arg Ala
    150                 155                 160

TAT ACT CAT GAA GTT GTC ACT TTA TGG TAT CGA GCT CCC GAA ATC TTG        582
Tyr Thr His Glu Val Val Thr Leu Trp Tyr Arg Ala Pro Glu Ile Leu
165                 170                 175                 180

TTA GGA GGG AAA CAA TAT TCC ACT GGG GTA GAT ATG TGG TCT GTT GGA        630
Leu Gly Gly Lys Gln Tyr Ser Thr Gly Val Asp Met Trp Ser Val Gly
                185                 190                 195
```

```
TGT ATA TTT GCT GAA ATG TGT AAT AGG AAA CCA TTA TTT CCT GGT GAT       678
Cys Ile Phe Ala Glu Met Cys Asn Arg Lys Pro Leu Phe Pro Gly Asp
            200             205             210

TCA GAA ATT GAT GAA ATT TTC CGA ATT TTC CGA ATT TTA GGA ACA CCT       726
Ser Glu Ile Asp Glu Ile Phe Arg Ile Phe Arg Ile Leu Gly Thr Pro
        215             220             225

AAT GAA GAA ATT TGG CCT GAT GTT AAT TAT TTA CCA GAT TTT AAA TCA       774
Asn Glu Glu Ile Trp Pro Asp Val Asn Tyr Leu Pro Asp Phe Lys Ser
    230             235             240

AGT TTC CCT CAA TGG AAA AAG AAA CCT TTG AGT GAA GCA GTT CCA AGT       822
Ser Phe Pro Gln Trp Lys Lys Lys Pro Leu Ser Glu Ala Val Pro Ser
245             250             255             260

TTG GAT GCT AAT GGA ATT GAT CTT TTG GAT CAA ATG TTG GTG TAT GAT       870
Leu Asp Ala Asn Gly Ile Asp Leu Leu Asp Gln Met Leu Val Tyr Asp
                265             270             275

CCA AGT AGA AGA ATA AGT GCT AAA CGA GCT TTA ATT CAT CCT TAT TTT       918
Pro Ser Arg Arg Ile Ser Ala Lys Arg Ala Leu Ile His Pro Tyr Phe
            280             285             290

AAT GAT AAT GAT GAT CGT GAT CAT AAC AAT TAT AAT GAA GAT AAT ATT       966
Asn Asp Asn Asp Asp Arg Asp His Asn Asn Tyr Asn Glu Asp Asn Ile
        295             300             305

GGG ATT GAC AAA CAC CAA AAC ATG CAA TAAATCTTG                        1002
Gly Ile Asp Lys His Gln Asn Met Gln
    310             315
```

( 2 ) INFORMATION FOR SEQ ID NO:4:

( i ) SEQUENCE CHARACTERISTICS:
        ( A ) LENGTH: 1752 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 184..1659

( x i ) SEQUENCE DESCRIPTION: SEQ ID NO:4:

```
GCTATTCCCC CCTTTTCCTT TTTTTTATAG AGAAACTTAT TCCAATTACT CATCGAACAA       60

GATCTTACTA GACTTGTAGA CTCACGACAC GATAAATTTT AATTCATTAA TCAACCAACG      120

AACCAGCCAA ACCAAAATTA ATTCACATTT ATACTCACTG TTTGTCATTT TCATCTCATA      180

GTA ATG CCA CAA GTC ACT AAA ACT AAT AAT GAA AAT GAG TTT AGA CTT       228
    Met Pro Gln Val Thr Lys Thr Asn Asn Glu Asn Glu Phe Arg Leu
    1               5              10              15

ACT AGA TCA AAA GTA CAG CAT CAA GAG TCG ATA AGT ACC ATC AAA AAT       276
Thr Arg Ser Lys Val Gln His Gln Glu Ser Ile Ser Thr Ile Lys Asn
            20              25              30

ACG ACC ATA TCC AAT TCT CAG CAT AAA CAA CAA ACA CAA CAA CAA ATT       324
Thr Thr Ile Ser Asn Ser Gln His Lys Gln Gln Thr Gln Gln Gln Ile
        35              40              45

TCA TCA CCA CCT CAA GTC TCT GTA ACA TCA TCT GAA GGA GTT TCA CAT       372
Ser Ser Pro Pro Gln Val Ser Val Thr Ser Ser Glu Gly Val Ser His
    50              55              60

GTC AAT ACA CGT CAA TAT TTG GGT GAT GTT TCA AAT CAA TAC ATA ACA       420
Val Asn Thr Arg Gln Tyr Leu Gly Asp Val Ser Asn Gln Tyr Ile Thr
65              70              75

AAT GCT AAA CCA ACA AAT AAA AGA AAA CCA TTG GGT GGA GAC AAT GCC       468
Asn Ala Lys Pro Thr Asn Lys Arg Lys Pro Leu Gly Gly Asp Asn Ala
80              85              90              95

CCT CTA CAA AAA CAA CAG CAT AGA CCA TCT AGA CCA ATA CCC ATT GCC       516
```

```
                                                -continued

Pro Leu Gln Lys Gln Gln His Arg Pro Ser Arg Pro Ile Pro Ile Ala
                100                 105                 110

AGT GAT AAC AAC AAT AAT GGT AGT ACC AGT AGC AGT AGC AAC AGT AGC    564
Ser Asp Asn Asn Asn Asn Gly Ser Thr Ser Ser Ser Ser Asn Ser Ser
            115                 120                 125

AAC AAC AAT AAC AAC GAC GCA AAT AGA CTA GCA TCT TTG GCA GTT CCA    612
Asn Asn Asn Asn Asn Asp Ala Asn Arg Leu Ala Ser Leu Ala Val Pro
        130                 135                 140

TCT CGA TTA CCC CAA AAA CGA CAA GCT ACT GAA TCG TCG ACA AAT TTA    660
Ser Arg Leu Pro Gln Lys Arg Gln Ala Thr Glu Ser Ser Thr Asn Leu
        145                 150                 155

GTA GAG AAA TTA AGA GTA CCA CAA CCA GAA GTA GGG GAA AGA AGT CAG    708
Val Glu Lys Leu Arg Val Pro Gln Pro Glu Val Gly Glu Arg Ser Gln
160                 165                 170                 175

TCA TAC CAT AAG AAA TCA CGT TTA ATT GAT TAT GAA TGG CAG GAT TTG    756
Ser Tyr His Lys Lys Ser Arg Leu Ile Asp Tyr Glu Trp Gln Asp Leu
                180                 185                 190

GAT GAA GAA GAT AAT GAC GAC CAA TTA ATG GTT AGT GAA TAT GTT AAC    804
Asp Glu Glu Asp Asn Asp Asp Gln Leu Met Val Ser Glu Tyr Val Asn
            195                 200                 205

GAA ATA TTT TCG TAC TAT TAC GAA TTA GAA ACA CGA ATG TTA CCT GAT    852
Glu Ile Phe Ser Tyr Tyr Tyr Glu Leu Glu Thr Arg Met Leu Pro Asp
        210                 215                 220

CCG CAA TAT CTT TTC AAA CAA ACA TTG TTA AAA CCA AGA ATG AGA TCG    900
Pro Gln Tyr Leu Phe Lys Gln Thr Leu Leu Lys Pro Arg Met Arg Ser
        225                 230                 235

ATA TTG GTT GAT TGG CTT GTT GAA ATG CAT TTA AAA TTC AAG TTA TTA    948
Ile Leu Val Asp Trp Leu Val Glu Met His Leu Lys Phe Lys Leu Leu
240                 245                 250                 255

CCT GAA TCA CTT TTT TTG GCA GTC AAT GTA ATG GAT AGA TTC ATG TCT    996
Pro Glu Ser Leu Phe Leu Ala Val Asn Val Met Asp Arg Phe Met Ser
                260                 265                 270

GTT GAA GTG GTT CAA ATA GAT AAA TTA CAA TTA TTG GCT ACA GCA GCT   1044
Val Glu Val Val Gln Ile Asp Lys Leu Gln Leu Leu Ala Thr Ala Ala
            275                 280                 285

TTA TTT ACT GCT GCC AAA AAT GAA GAA GTA TTT TCT CCC CTG GTT AAA   1092
Leu Phe Thr Ala Ala Lys Asn Glu Glu Val Phe Ser Pro Ser Val Lys
        290                 295                 300

AAT TAT GCA TAT TTC ACT GAT GGT TCA TAT ACT CCA GAA GAA GTG GTA   1140
Asn Tyr Ala Tyr Phe Thr Asp Gly Ser Tyr Thr Pro Glu Glu Val Val
        305                 310                 315

CAA GCA GAA AAA TAC ATG CTT ACC ATT CTT AAC TTT GAT TTG AAT TAC   1188
Gln Ala Glu Lys Tyr Met Leu Thr Ile Leu Asn Phe Asp Leu Asn Tyr
320                 325                 330                 335

CCC AAT CCA ATG AAT TTC TTG AGA AGA ATT TCT AAA GCT GAT GAT TAT   1236
Pro Asn Pro Met Asn Phe Leu Arg Arg Ile Ser Lys Ala Asp Asp Tyr
                340                 345                 350

GAT GTC CAA TCA AGA ACG CTA GGA AAA TAT CTT TTG GAA ATC ACT ATA   1284
Asp Val Gln Ser Arg Thr Leu Gly Lys Tyr Leu Leu Glu Ile Thr Ile
            355                 360                 365

GTT GAT TAC AAA TTT ATT GGT ATG AGA CCA TCT TTA TGT TGT GCC CTG   1332
Val Asp Tyr Lys Phe Ile Gly Met Arg Pro Ser Leu Cys Cys Ala Leu
        370                 375                 380

GCC ATG TAT TTA GCA AGA CTA ATA TTG GGC AAA TTG CCA GTT TGG AAT   1380
Ala Met Tyr Leu Ala Arg Leu Ile Leu Gly Lys Leu Pro Val Trp Asn
        385                 390                 395

GGG AAT TTG ATT CAT TAT AGT GGA GGT TAT AGA ATC AGT GAT ATG AGA   1428
Gly Asn Leu Ile His Tyr Ser Gly Gly Tyr Arg Ile Ser Asp Met Arg
400                 405                 410                 415

GAA TGT ATC GAA TTA ATG TTT CAA TAT CTT ATT GCT CCT ATA GAA CAT   1476
```

```
Glu  Cys  Ile  Glu  Leu  Met  Phe  Gln  Tyr  Leu  Ile  Ala  Pro  Ile  Glu  His
               420                 425                      430

GAT  GAA  TTT  TTC  AAA  AAA  TAT  GCC  ATG  AGA  AAA  TTT  ATG  AGA  GCA  AGT    1524
Asp  Glu  Phe  Phe  Lys  Lys  Tyr  Ala  Met  Arg  Lys  Phe  Met  Arg  Ala  Ser
               435                 440                      445

ACT  CTT  TGT  CGA  AAT  TGG  GCT  AAA  AAA  TTC  CAA  GCA  TCA  GGA  AGA  GAT    1572
Thr  Leu  Cys  Arg  Asn  Trp  Ala  Lys  Lys  Phe  Gln  Ala  Ser  Gly  Arg  Asp
               450                 455                      460

TTG  TTT  GAT  GAA  CGA  TTA  TCG  ACC  CAT  AGG  CTA  ACA  TTA  GAA  GAT  GAT    1620
Leu  Phe  Asp  Glu  Arg  Leu  Ser  Thr  His  Arg  Leu  Thr  Leu  Glu  Asp  Asp
          465                      470                 475

GAC  GAA  GAA  GAA  GAA  ATA  GTG  GTA  GCA  GAA  GCA  GAA  GAG  TAAAGTTTTG        1669
Asp  Glu  Glu  Glu  Glu  Ile  Val  Val  Ala  Glu  Ala  Glu  Glu
480                      485                      490

AGGACTATTG  GATCTAGGTT  CTTATCTTTA  CAATGCATAA  ATGAGGAAAT  GAAAGAAGAT             1729

GAACATGAGT  TATGTGCATT  ACC                                                        1752
```

( 2 ) INFORMATION FOR SEQ ID NO:5:

( i ) SEQUENCE CHARACTERISTICS:
        ( A ) LENGTH: 1070 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 30..1058

( x i ) SEQUENCE DESCRIPTION: SEQ ID NO:5:

```
ATCAAATCCA  TCAGAGAACC  ACATCAATC  ATG  TCT  ACT  GCA  GCA  GTT  GCA  ACG          53
                                  Met  Ser  Thr  Ala  Ala  Val  Ala  Thr
                                   1                  5

AAA  CCA  TCT  GTC  ACT  TCA  AAA  CCA  GCA  ACT  AAA  CAA  GTT  CTG  AAT  TAC    101
Lys  Pro  Ser  Val  Thr  Ser  Lys  Pro  Ala  Thr  Lys  Gln  Val  Leu  Asn  Tyr
          10                       15                      20

ACC  AAA  GAA  AAA  AAA  GTA  GGG  GAA  GGT  ACA  TAT  GCT  GTT  GTG  TAC  TTG    149
Thr  Lys  Glu  Lys  Lys  Val  Gly  Glu  Gly  Thr  Tyr  Ala  Val  Val  Tyr  Leu
25                       30                      35                           40

GGT  AAA  CAA  ATC  TCC  ACC  AAA  CGT  CAA  ATT  GCC  ATC  AAA  GAA  ATC  AAA    197
Gly  Lys  Gln  Ile  Ser  Thr  Lys  Arg  Gln  Ile  Ala  Ile  Lys  Glu  Ile  Lys
               45                       50                      55

ACA  GGA  TTA  TTC  AAA  GAT  GGG  TTG  GAT  ATG  TCA  GCA  TTG  AGA  GAA  GTG    245
Thr  Gly  Leu  Phe  Lys  Asp  Gly  Leu  Asp  Met  Ser  Ala  Leu  Arg  Glu  Val
               60                       65                      70

AAA  TAT  TTG  CAA  GAA  TTG  AAA  CAT  CCC  AAT  GTT  ATT  GAA  CTA  GTA  GAT    293
Lys  Tyr  Leu  Gln  Glu  Leu  Lys  His  Pro  Asn  Val  Ile  Glu  Leu  Val  Asp
          75                       80                      85

GTA  TTT  TCA  GCA  ACA  AAT  AAT  TTA  AAT  TTG  GTA  TTA  GAA  TTT  CTA  CCT    341
Val  Phe  Ser  Ala  Thr  Asn  Asn  Leu  Asn  Leu  Val  Leu  Glu  Phe  Leu  Pro
          90                       95                      100

TGC  GAT  TTG  GAA  GTG  TTG  ATC  AAA  GAT  AAA  TCG  ATT  GTT  TTC  AAA  TCA    389
Cys  Asp  Leu  Glu  Val  Leu  Ile  Lys  Asp  Lys  Ser  Ile  Val  Phe  Lys  Ser
105                      110                     115                          120

GCA  GAT  ATC  AAA  TCA  TGG  CTT  TTA  ATG  ACA  TTA  CGT  GGG  ATA  CAT  CAT    437
Ala  Asp  Ile  Lys  Ser  Trp  Leu  Leu  Met  Thr  Leu  Arg  Gly  Ile  His  His
               125                      130                     135

TGT  CAT  CGG  AAT  TTT  ATT  TTA  CAT  CGT  GAT  TTG  AAA  CCA  AAT  AAT  TTA    485
Cys  His  Arg  Asn  Phe  Ile  Leu  His  Arg  Asp  Leu  Lys  Pro  Asn  Asn  Leu
               140                      145                     150
```

| | | | | | | | | | | | | | | | | |
|---|---|---|---|---|---|---|---|---|---|---|---|---|---|---|---|---|
|TTA|TTG|GCA|CCG|GAT|GGA|CAA|TTG|AAA|ATA|GCG|GAT|TTT|GGT|CTT|GCA|533|
|Leu|Leu|Ala|Pro|Asp|Gly|Gln|Leu|Lys|Ile|Ala|Asp|Phe|Gly|Leu|Ala| |
| | |155| | | |160| | | |165| | | | | | |
|CGA|GCT|TTG|GTA|AAT|CCT|AAT|GAA|GAT|TTA|TCA|TCT|AAT|GTT|GTC|ACT|581|
|Arg|Ala|Leu|Val|Asn|Pro|Asn|Glu|Asp|Leu|Ser|Ser|Asn|Val|Val|Thr| |
| |170| | | |175| | | |180| | | | | | | |
|AGA|TGG|TAT|AGA|GCC|CCT|GAA|TTA|TTA|TTT|GGT|GCT|CGA|CAT|TAC|ACT|629|
|Arg|Trp|Tyr|Arg|Ala|Pro|Glu|Leu|Leu|Phe|Gly|Ala|Arg|His|Tyr|Thr| |
|185| | | | |190| | | |195| | | | |200| | |
|GGA|GCA|GTT|GAT|ATC|TGG|TCA|ATA|GGT|ATA|ATA|TTT|GCT|GAA|TTA|ATG|677|
|Gly|Ala|Val|Asp|Ile|Trp|Ser|Ile|Gly|Ile|Ile|Phe|Ala|Glu|Leu|Met| |
| | | | |205| | | | |210| | | | |215| | |
|CTT|CGA|ATA|CCT|TAT|TTG|CCA|GGT|AAA|GAT|GAC|GTT|GAT|CAA|TTA|GAT|725|
|Leu|Arg|Ile|Pro|Tyr|Leu|Pro|Gly|Lys|Asp|Asp|Val|Asp|Gln|Leu|Asp| |
| | | |220| | | | |225| | | | |230| | | |
|GTT|ACA|TTT|AGA|GCT|TAT|GGG|ACA|CCA|ACA|GAG|CAA|ATA|TGG|CCA|AAT|773|
|Val|Thr|Phe|Arg|Ala|Tyr|Gly|Thr|Pro|Thr|Glu|Gln|Ile|Trp|Pro|Asn| |
| | |235| | | | |240| | | | |245| | | | |
|GTT|TCC|AGT|TTG|CCA|ATG|TAT|AAT|GCA|CTT|CAT|GTG|TAT|CCA|CCT|CCT|821|
|Val|Ser|Ser|Leu|Pro|Met|Tyr|Asn|Ala|Leu|His|Val|Tyr|Pro|Pro|Pro| |
| |250| | | | |255| | | | |260| | | | | |
|TCA|AGA|CAA|GAA|TTA|CGT|AAT|AGA|TTT|AGT|GCT|GCT|ACG|GAA|AAA|GCC|869|
|Ser|Arg|Gln|Glu|Leu|Arg|Asn|Arg|Phe|Ser|Ala|Ala|Thr|Glu|Lys|Ala| |
|265| | | | |270| | | | |275| | | | |280| |
|CTT|GAT|TTG|TTG|ATA|TCG|ATG|ACC|CAA|TTG|GAT|CCA|AGT|AGA|AGA|TGT|917|
|Leu|Asp|Leu|Leu|Ile|Ser|Met|Thr|Gln|Leu|Asp|Pro|Ser|Arg|Arg|Cys| |
| | | | |285| | | | |290| | | | |295| | |
|GAT|TCT|ACA|CTA|GCA|TTA|TTA|CAC|GAT|TAT|TTT|ACT|GAA|TCG|CCT|CGT|965|
|Asp|Ser|Thr|Leu|Ala|Leu|Leu|His|Asp|Tyr|Phe|Thr|Glu|Ser|Pro|Arg| |
| | | |300| | | | |305| | | | |310| | | |
|CCT|ACT|GAC|CCG|AAA|AAG|TTG|CCT|AAA|AAG|TCT|TCT|CCA|GAA|AAG|AGA|1013|
|Pro|Thr|Asp|Pro|Lys|Lys|Leu|Pro|Lys|Lys|Ser|Ser|Pro|Glu|Lys|Arg| |
| | |315| | | | |320| | | | |325| | | | |
|GAA|AAT|GAA|GAT|GAA|CAG|AAT|AAT|GGC|TCT|AAA|AGA|AGG|CAT|GTT| |1058|
|Glu|Asn|Glu|Asp|Glu|Gln|Asn|Asn|Gly|Ser|Lys|Arg|Arg|His|Val| | |
| |330| | | | |335| | | | |340| | | | | |
|TAGGTTTCTA TA| | | | | | | | | | | | | | | |1070|

( 2 ) INFORMATION FOR SEQ ID NO:6:

( i ) SEQUENCE CHARACTERISTICS:
        ( A ) LENGTH: 477 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..477

( x i ) SEQUENCE DESCRIPTION: SEQ ID NO:6:

| | | | | | | | | | | | | | | | | |
|---|---|---|---|---|---|---|---|---|---|---|---|---|---|---|---|---|
|TGT|TCA|GCT|ATT|GAT|ACG|AAA|AGT|TCA|GTC|TCA|GCG|ATG|GAG|CAC|AAG|48|
|Cys|Ser|Ala|Ile|Asp|Thr|Lys|Ser|Ser|Val|Ser|Ala|Met|Glu|His|Lys| |
|1| | | |5| | | | |10| | | | |15| | |
|ATT|GCT|ATA|AAG|AAA|GTA|ACA|AAG|ATT|TTC|AAC|AAA|GAC|ATC|CTT|CTA|96|
|Ile|Ala|Ile|Lys|Lys|Val|Thr|Lys|Ile|Phe|Asn|Lys|Asp|Ile|Leu|Leu| |
| | | |20| | | | |25| | | | |30| | | |
|ATC|AGG|GCA|ATA|CGA|GAG|CTT|AAG|TTC|ATG|ATG|TTT|TTC|AGA|GGC|CAC|144|
|Ile|Arg|Ala|Ile|Arg|Glu|Leu|Lys|Phe|Met|Met|Phe|Phe|Arg|Gly|His| |
| | |35| | | | |40| | | | |45| | | | |
|AAG|AAT|ATT|GCA|ACT|TTG|CTT|GAC|TTA|GAT|GTT|GTA|TAT|GTG|AAG|CCT|192|

|       |       |       |       |       |       |       |       |       |       |       |       |       |       |       |       |     |
|-------|-------|-------|-------|-------|-------|-------|-------|-------|-------|-------|-------|-------|-------|-------|-------|-----|
| Lys   | Asn   | Ile   | Ala   | Thr   | Leu   | Leu   | Asp   | Leu   | Asp   | Val   | Val   | Tyr   | Val   | Lys   | Pro   |     |
|       | 50    |       |       |       |       | 55    |       |       |       | 60    |       |       |       |       |       |     |
| TAT   | GAA   | GGC   | TTG   | TAT   | TGT   | TTT   | CAA   | GAG   | CTA   | GCC   | GAT   | TTA   | GAT   | TTA   | GCT   | 240 |
| Tyr   | Glu   | Gly   | Leu   | Tyr   | Cys   | Phe   | Gln   | Glu   | Leu   | Ala   | Asp   | Leu   | Asp   | Leu   | Ala   |     |
| 65    |       |       |       |       | 70    |       |       |       |       | 75    |       |       |       |       | 80    |     |
| CGT   | GTT   | TTG   | TAC   | TCA   | AAC   | GTC   | CAA   | TTT   | TCA   | GAA   | TTT   | CAC   | ATT   | CAA   | AGC   | 288 |
| Arg   | Val   | Leu   | Tyr   | Ser   | Asn   | Val   | Gln   | Phe   | Ser   | Glu   | Phe   | His   | Ile   | Gln   | Ser   |     |
|       |       |       |       | 85    |       |       |       |       | 90    |       |       |       |       | 95    |       |     |
| TTT   | ATG   | TAC   | CAA   | ATT   | CTT   | TGC   | GGA   | CTC   | AAG   | TAC   | ATC   | CAT   | TCT   | GCT   | GAT   | 336 |
| Phe   | Met   | Tyr   | Gln   | Ile   | Leu   | Cys   | Gly   | Leu   | Lys   | Tyr   | Ile   | His   | Ser   | Ala   | Asp   |     |
|       |       |       | 100   |       |       |       |       | 105   |       |       |       | 110   |       |       |       |     |
| GTA   | ATA   | CAT   | CGG   | GAC   | CTA   | AAG   | CCA   | GGA   | AAC   | ATA   | TTG   | GTC   | ACC   | ACT   | CAA   | 384 |
| Val   | Ile   | His   | Arg   | Asp   | Leu   | Lys   | Pro   | Gly   | Asn   | Ile   | Leu   | Val   | Thr   | Thr   | Gln   |     |
|       |       | 115   |       |       |       |       | 120   |       |       |       |       | 125   |       |       |       |     |
| GGG   | ACT   | TTA   | AAA   | ATA   | TGT   | GAT   | TTC   | GGC   | TTA   | GCA   | CGA   | GGA   | ATA   | AAT   | CCT   | 432 |
| Gly   | Thr   | Leu   | Lys   | Ile   | Cys   | Asp   | Phe   | Gly   | Leu   | Ala   | Arg   | Gly   | Ile   | Asn   | Pro   |     |
|       | 130   |       |       |       |       | 135   |       |       |       |       | 140   |       |       |       |       |     |
| GTA   | TAT   | TTC   | AGA   | AAC   | CGC   | TCA   | GCT   | GTC   | ATC   | ACA   | AAC   | TAC   | GTA   | GCA   |       | 477 |
| Val   | Tyr   | Phe   | Arg   | Asn   | Arg   | Ser   | Ala   | Val   | Ile   | Thr   | Asn   | Tyr   | Val   | Ala   |       |     |
| 145   |       |       |       |       | 150   |       |       |       |       | 155   |       |       |       |       |       |     |

( 2 ) INFORMATION FOR SEQ ID NO:7:

( i ) SEQUENCE CHARACTERISTICS:
        ( A ) LENGTH: 411 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

|     |     |     |     |     |     |     |     |     |     |     |     |     |     |     |
|-----|-----|-----|-----|-----|-----|-----|-----|-----|-----|-----|-----|-----|-----|-----|
| Met | Thr | Glu | Val | Val | Ser | Lys | Ser | Ser | His | Ser | Phe | Phe | Asn | Asn | Leu |
| 1   |     |     |     | 5   |     |     |     |     | 10  |     |     |     |     | 15  |     |
| His | Leu | Ala | Thr | Ser | Thr | Ala | Ser | Ser | Val | Ser | Ser | Thr | Thr | Pro |     |
|     |     |     | 20  |     |     |     |     | 25  |     |     |     |     | 30  |     |     |
| Lys | Ile | Glu | Phe | Asn | Ser | Ile | Ala | Glu | Asn | Asp | Asp | Ile | Pro | Thr | Asn |
|     |     |     | 35  |     |     |     |     | 40  |     |     |     |     | 45  |     |     |
| Tyr | Asp | Ser | Asp | Glu | Glu | Phe | Glu | Asp | Gly | Asp | Thr | Phe | Ile | Gln | Ser |
|     | 50  |     |     |     |     | 55  |     |     |     |     | 60  |     |     |     |     |
| Thr | Leu | Ile | His | Gln | Phe | Asn | Ala | Ser | Gln | Val | Thr | Thr | Thr | Thr | Ile |
| 65  |     |     |     |     | 70  |     |     |     |     | 75  |     |     |     |     | 80  |
| Ile | Ile | Ile | Pro | Met | Met | Val | Thr | Thr | Ile | Ile | Tyr | Leu | Gln | Lys | Leu |
|     |     |     |     | 85  |     |     |     |     | 90  |     |     |     |     | 95  |     |
| Asp | Gly | Ser | Thr | Pro | Cys | Thr | Lys | Pro | Ile | Lys | Arg | Leu | His | Arg | Thr |
|     |     |     | 100 |     |     |     |     | 105 |     |     |     |     | 110 |     |     |
| Asn | Phe | Met | Lys | Ile | Ile | His | Phe | Glu | Ile | Tyr | Asn | Ile | Glu | Tyr | Ser |
|     |     |     | 115 |     |     |     |     | 120 |     |     |     |     | 125 |     |     |
| His | Leu | Glu | Ser | Asp | Leu | Leu | Pro | Arg | Ile | Asp | Ala | His | Gln | Leu | Ala |
|     |     | 130 |     |     |     |     | 135 |     |     |     |     | 140 |     |     |     |
| Arg | Ile | Leu | Arg | Gly | Asp | His | Asp | Asp | Gln | Phe | Asp | Glu | Phe | Ile | Ile |
| 145 |     |     |     |     | 150 |     |     |     |     | 155 |     |     |     |     | 160 |
| Ile | Asp | Cys | Arg | Phe | Glu | Tyr | Glu | Phe | Asn | Gly | Gly | His | Ile | Thr | Arg |
|     |     |     |     | 165 |     |     |     |     | 170 |     |     |     |     | 175 |     |
| Ala | Ile | Asn | Ile | Ser | Thr | Gln | Glu | Ala | Leu | Gln | Glu | Lys | Leu | Phe | Gln |
|     |     |     | 180 |     |     |     |     | 185 |     |     |     |     | 190 |     |     |
| Tyr | Gln | Glu | Thr | Asp | Thr | Lys | Asp | Thr | Glu | Ser | Lys | Lys | Arg | Leu | Ile |
|     |     |     | 195 |     |     |     |     | 200 |     |     |     |     | 205 |     |     |
| Ile | Phe | His | Cys | Glu | Phe | Ser | Met | Phe | Arg | Gly | Pro | Met | Met | Ala | Lys |
|     |     | 210 |     |     |     |     | 215 |     |     |     |     | 220 |     |     |     |

His Leu Arg Lys Cys Asp Arg Met Cys Asn Tyr Asp Asn Tyr Pro Leu
225                 230                 235                 240

Leu Thr Tyr Pro Asp Ile Ala Ile Leu Glu Gly Gly Tyr Lys Asn Phe
            245                 250                 255

Tyr Glu Asn Tyr Pro Gln Trp Cys Asp Pro Gln Gly Tyr Val Glu Met
            260                 265                 270

Lys Asn Leu Arg His Lys Lys Leu Cys Glu Ser Asn Leu Asp Lys Val
        275                 280                 285

Arg Lys Asp Asn Lys Leu Thr Arg Ala Lys Ser Tyr Gln Phe Gly Ile
    290                 295                 300

Gln His Arg Arg Gly Gly Ser Thr Gly Gly Leu Phe Gly Asn Tyr Asn
305                 310                 315                 320

Tyr Asn Val Met Asn Ser Ser Asp Gln Gln Phe Trp Ser Ser Ser Thr
                325                 330                 335

Ser Asn Thr Ala His His Arg Ser Ser Ser Ser Gly Phe Ile Asn
            340                 345                 350

Asn Met His Ser Gly Ala Ser Ser Tyr His His Arg Ser Gln Ser Phe
        355                 360                 365

Val Thr Ile Asn Asn Glu Lys Ile Ile Lys Arg Gln Arg Ser Thr Pro
370                 375                 380

Lys Val Ser Asn Ser Pro Thr Lys Pro Pro His Gln Leu Tyr Leu Leu
385                 390                 395                 400

Ile Asn Pro Phe Arg Trp Leu Ile Phe Ile Asp
            405                 410

( 2 ) INFORMATION FOR SEQ ID NO:8:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Met Thr Lys Pro Arg Phe Leu Thr Arg Tyr Arg Lys Ser Lys Ser Val
1               5                   10                  15

Gly Ile Ser Asp Met Ile His Tyr Ser Pro Arg Tyr Ser Asp Asp Ser
            20                  25                  30

Tyr Glu Tyr Arg His Val Met Leu Pro Lys Asn Met Leu Lys Ala Ile
        35                  40                  45

Pro His Asp Tyr Phe Asn Gln Glu Thr Gly Thr Leu Arg Ile Leu Thr
    50                  55                  60

Glu Glu Glu Trp Arg Gly Leu Gly Ile Thr Gln Ser Leu Gly Trp Ala
65                  70                  75                  80

His Tyr Glu Thr His Ala Pro Glu Pro His Ile Leu Leu Phe Lys Arg
                85                  90                  95

Pro Leu Asn Pro Gly Gln
            100

( 2 ) INFORMATION FOR SEQ ID NO:9:

( i ) SEQUENCE CHARACTERISTICS:
        ( A ) LENGTH: 317 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met | Val | Glu | Leu | Ser | Asp | Tyr | Gln | Arg | Gln | Glu | Lys | Val | Gly | Glu | Gly |
| 1 | | | | 5 | | | | | 10 | | | | | 15 | |
| Thr | Tyr | Gly | Val | Val | Tyr | Lys | Ala | Leu | Asp | Thr | Lys | His | Asn | Asn | Arg |
| | | | 20 | | | | 25 | | | | | 30 | | | |
| Val | Val | Ala | Leu | Lys | Lys | Ile | Arg | Leu | Glu | Ser | Glu | Asp | Glu | Gly | Val |
| | | 35 | | | | 40 | | | | | 45 | | | | |
| Pro | Ser | Thr | Ala | Ile | Arg | Glu | Ile | Ser | Leu | Leu | Lys | Glu | Met | Lys | Asp |
| | 50 | | | | | 55 | | | | | 60 | | | | |
| Asp | Asn | Ile | Val | Arg | Leu | Tyr | Asp | Ile | Ile | His | Ser | Asp | Ser | His | Lys |
| 65 | | | | | 70 | | | | | 75 | | | | | 80 |
| Leu | Tyr | Leu | Val | Phe | Glu | Phe | Leu | Asp | Leu | Asp | Leu | Lys | Lys | Tyr | Met |
| | | | | 85 | | | | | 90 | | | | | 95 | |
| Glu | Ser | Ile | Pro | Gln | Gly | Val | Gly | Leu | Gly | Ala | Asn | Met | Ile | Lys | Arg |
| | | | 100 | | | | | 105 | | | | | 110 | | |
| Phe | Met | Asn | Gln | Leu | Ile | Arg | Gly | Ile | Lys | His | Cys | His | Ser | His | Arg |
| | | 115 | | | | | 120 | | | | | 125 | | | |
| Val | Leu | His | Arg | Asp | Leu | Lys | Pro | Gln | Asn | Leu | Leu | Ile | Asp | Lys | Glu |
| | 130 | | | | | 135 | | | | | 140 | | | | |
| Gly | Asn | Leu | Lys | Leu | Ala | Asp | Phe | Gly | Leu | Ala | Arg | Ala | Phe | Gly | Val |
| 145 | | | | | 150 | | | | | 155 | | | | | 160 |
| Pro | Leu | Arg | Ala | Tyr | Thr | His | Glu | Val | Val | Thr | Leu | Trp | Tyr | Arg | Ala |
| | | | | 165 | | | | | 170 | | | | | 175 | |
| Pro | Glu | Ile | Leu | Leu | Gly | Gly | Lys | Gln | Tyr | Ser | Thr | Gly | Val | Asp | Met |
| | | | | 180 | | | | | 185 | | | | | 190 | |
| Trp | Ser | Val | Gly | Cys | Ile | Phe | Ala | Glu | Met | Cys | Asn | Arg | Lys | Pro | Leu |
| | | 195 | | | | | 200 | | | | | 205 | | | |
| Phe | Pro | Gly | Asp | Ser | Glu | Ile | Asp | Glu | Ile | Phe | Arg | Ile | Phe | Arg | Ile |
| | 210 | | | | | 215 | | | | | 220 | | | | |
| Leu | Gly | Thr | Pro | Asn | Glu | Glu | Ile | Trp | Pro | Asp | Val | Asn | Tyr | Leu | Pro |
| 225 | | | | | 230 | | | | | 235 | | | | | 240 |
| Asp | Phe | Lys | Ser | Ser | Phe | Pro | Gln | Trp | Lys | Lys | Lys | Pro | Leu | Ser | Glu |
| | | | | 245 | | | | | 250 | | | | | 255 | |
| Ala | Val | Pro | Ser | Leu | Asp | Ala | Asn | Gly | Ile | Asp | Leu | Leu | Asp | Gln | Met |
| | | | 260 | | | | | 265 | | | | | 270 | | |
| Leu | Val | Tyr | Asp | Pro | Ser | Arg | Arg | Ile | Ser | Ala | Lys | Arg | Ala | Leu | Ile |
| | | 275 | | | | | 280 | | | | | 285 | | | |
| His | Pro | Tyr | Phe | Asn | Asp | Asn | Asp | Asp | Arg | Asp | His | Asn | Asn | Tyr | Asn |
| | 290 | | | | | 295 | | | | | 300 | | | | |
| Glu | Asp | Asn | Ile | Gly | Ile | Asp | Lys | His | Gln | Asn | Met | Gln | | | |
| 305 | | | | 310 | | | | | 315 | | | | | | |

( 2 ) INFORMATION FOR SEQ ID NO:10:

( i ) SEQUENCE CHARACTERISTICS:
        ( A ) LENGTH: 492 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Met | Pro | Gln | Val | Thr | Lys | Thr | Asn | Asn | Glu | Asn | Glu | Phe | Arg | Leu | Thr |
| 1 | | | | 5 | | | | | 10 | | | | | 15 | |
| Arg | Ser | Lys | Val | Gln | His | Gln | Glu | Ser | Ile | Ser | Thr | Ile | Lys | Asn | Thr |
| | | | 20 | | | | 25 | | | | | 30 | | | |

```
Thr Ile Ser Asn Ser Gln His Lys Gln Gln Thr Gln Gln Ile Ser
        35              40                  45
Ser Pro Pro Gln Val Ser Val Thr Ser Ser Glu Gly Val Ser His Val
    50              55                  60
Asn Thr Arg Gln Tyr Leu Gly Asp Val Ser Asn Gln Tyr Ile Thr Asn
65                  70              75                      80
Ala Lys Pro Thr Asn Lys Arg Lys Pro Leu Gly Gly Asp Asn Ala Pro
            85              90                      95
Leu Gln Lys Gln Gln His Arg Pro Ser Arg Pro Ile Pro Ile Ala Ser
            100             105             110
Asp Asn Asn Asn Asn Gly Ser Thr Ser Ser Ser Ser Asn Ser Ser Asn
            115             120             125
Asn Asn Asn Asn Asp Ala Asn Arg Leu Ala Ser Leu Ala Val Pro Ser
        130             135             140
Arg Leu Pro Gln Lys Arg Gln Ala Thr Glu Ser Ser Thr Asn Leu Val
145             150             155                         160
Glu Lys Leu Arg Val Pro Gln Pro Glu Val Gly Glu Arg Ser Gln Ser
                165             170                 175
Tyr His Lys Lys Ser Arg Leu Ile Asp Tyr Glu Trp Gln Asp Leu Asp
            180             185                 190
Glu Glu Asp Asn Asp Asp Gln Leu Met Val Ser Glu Tyr Val Asn Glu
        195             200             205
Ile Phe Ser Tyr Tyr Tyr Glu Leu Glu Thr Arg Met Leu Pro Asp Pro
    210             215             220
Gln Tyr Leu Phe Lys Gln Thr Leu Leu Lys Pro Arg Met Arg Ser Ile
225             230             235                         240
Leu Val Asp Trp Leu Val Glu Met His Leu Lys Phe Lys Leu Leu Pro
            245             250             255
Glu Ser Leu Phe Leu Ala Val Asn Val Met Asp Arg Phe Met Ser Val
            260             265             270
Glu Val Val Gln Ile Asp Lys Leu Gln Leu Leu Ala Thr Ala Ala Leu
        275             280             285
Phe Thr Ala Ala Lys Asn Glu Glu Val Phe Ser Pro Leu Val Lys Asn
290                 295             300
Tyr Ala Tyr Phe Thr Asp Gly Ser Tyr Thr Pro Glu Glu Val Val Gln
305             310             315                         320
Ala Glu Lys Tyr Met Leu Thr Ile Leu Asn Phe Asp Leu Asn Tyr Pro
            325             330             335
Asn Pro Met Asn Phe Leu Arg Arg Ile Ser Lys Ala Asp Asp Tyr Asp
            340             345             350
Val Gln Ser Arg Thr Leu Gly Lys Tyr Leu Leu Glu Ile Thr Ile Val
            355             360             365
Asp Tyr Lys Phe Ile Gly Met Arg Pro Ser Leu Cys Cys Ala Leu Ala
370             375                 380
Met Tyr Leu Ala Arg Leu Ile Leu Gly Lys Leu Pro Val Trp Asn Gly
385                 390             395                     400
Asn Leu Ile His Tyr Ser Gly Gly Tyr Arg Ile Ser Asp Met Arg Glu
            405             410             415
Cys Ile Glu Leu Met Phe Gln Tyr Leu Ile Ala Pro Ile Glu His Asp
            420             425             430
Glu Phe Phe Lys Lys Tyr Ala Met Arg Lys Phe Met Arg Ala Ser Thr
        435             440             445
Leu Cys Arg Asn Trp Ala Lys Lys Phe Gln Ala Ser Gly Arg Asp Leu
450                 455             460
```

Phe Asp Glu Arg Leu Ser Thr His Arg Leu Thr Leu Glu Asp Asp Asp
465                 470                 475                 480

Glu Glu Glu Glu Ile Val Val Ala Glu Ala Glu Glu
                485                 490

( 2 ) INFORMATION FOR SEQ ID NO:11:

( i ) SEQUENCE CHARACTERISTICS:
    ( A ) LENGTH: 343 amino acids
    ( B ) TYPE: amino acid
    ( D ) TOPOLOGY: linear ( i i ) MOLECULE TYPE: protein ( x i ) SEQUENCE DESCRIPTION: SEQ ID NO:11:

Met Ser Thr Ala Ala Val Ala Thr Lys Pro Ser Val Thr Ser Lys Pro
1               5                   10                  15

Ala Thr Lys Gln Val Leu Asn Tyr Thr Lys Glu Lys Lys Val Gly Glu
            20                  25                  30

Gly Thr Tyr Ala Val Val Tyr Leu Gly Lys Gln Ile Ser Thr Lys Arg
        35                  40                  45

Gln Ile Ala Ile Lys Glu Ile Lys Thr Gly Leu Phe Lys Asp Gly Leu
    50                  55                  60

Asp Met Ser Ala Leu Arg Glu Val Lys Tyr Leu Gln Glu Leu Lys His
65                  70                  75                  80

Pro Asn Val Ile Glu Leu Val Asp Val Phe Ser Ala Thr Asn Asn Leu
                85                  90                  95

Asn Leu Val Leu Glu Phe Leu Pro Cys Asp Leu Glu Val Leu Ile Lys
            100                 105                 110

Asp Lys Ser Ile Val Phe Lys Ser Ala Asp Ile Lys Ser Trp Leu Leu
        115                 120                 125

Met Thr Leu Arg Gly Ile His His Cys His Arg Asn Phe Ile Leu His
130                 135                 140

Arg Asp Leu Lys Pro Asn Asn Leu Leu Leu Ala Pro Asp Gly Gln Leu
145                 150                 155                 160

Lys Ile Ala Asp Phe Gly Leu Ala Arg Ala Leu Val Asn Pro Asn Glu
                165                 170                 175

Asp Leu Ser Ser Asn Val Val Thr Arg Trp Tyr Arg Ala Pro Glu Leu
            180                 185                 190

Leu Phe Gly Ala Arg His Tyr Thr Gly Ala Val Asp Ile Trp Ser Ile
        195                 200                 205

Gly Ile Ile Phe Ala Glu Leu Met Leu Arg Ile Pro Tyr Leu Pro Gly
210                 215                 220

Lys Asp Asp Val Asp Gln Leu Asp Val Thr Phe Arg Ala Tyr Gly Thr
225                 230                 235                 240

Pro Thr Glu Gln Ile Trp Pro Asn Val Ser Ser Leu Pro Met Tyr Asn
                245                 250                 255

Ala Leu His Val Tyr Pro Pro Pro Ser Arg Gln Glu Leu Arg Asn Arg
            260                 265                 270

Phe Ser Ala Ala Thr Glu Lys Ala Leu Asp Leu Leu Ile Ser Met Thr
        275                 280                 285

Gln Leu Asp Pro Ser Arg Arg Cys Asp Ser Thr Leu Ala Leu Leu His
290                 295                 300

Asp Tyr Phe Thr Glu Ser Pro Arg Pro Thr Asp Pro Lys Lys Leu Pro
305                 310                 315                 320

Lys Lys Ser Ser Pro Glu Lys Arg Glu Asn Glu Asp Glu Gln Asn Asn (2) INFORMATION FOR SEQ ID NO:12:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:12:

```
Cys Ser Ala Ile Asp Thr Lys Ser Ser Val Ser Ala Met Glu His Lys
  1               5                  10                  15
Ile Ala Ile Lys Lys Val Thr Lys Ile Phe Asn Lys Asp Ile Leu Leu
             20                  25                  30
Ile Arg Ala Ile Arg Glu Leu Lys Phe Met Met Phe Phe Arg Gly His
         35                  40                  45
Lys Asn Ile Ala Thr Leu Leu Asp Leu Asp Val Val Tyr Val Lys Pro
     50                  55                  60
Tyr Glu Gly Leu Tyr Cys Phe Gln Glu Leu Ala Asp Leu Asp Leu Ala
 65                  70                  75                  80
Arg Val Leu Tyr Ser Asn Val Gln Phe Ser Glu Phe His Ile Gln Ser
                 85                  90                  95
Phe Met Tyr Gln Ile Leu Cys Gly Leu Lys Tyr Ile His Ser Ala Asp
            100                 105                 110
Val Ile His Arg Asp Leu Lys Pro Gly Asn Ile Leu Val Thr Thr Gln
        115                 120                 125
Gly Thr Leu Lys Ile Cys Asp Phe Gly Leu Ala Arg Gly Ile Asn Pro
    130                 135                 140
Val Tyr Phe Arg Asn Arg Ser Ala Val Ile Thr Asn Tyr Val Ala
145                 150                 155
```

(2) INFORMATION FOR SEQ ID NO:13:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

```
ATGGATCCYT TRTANCCNCC RTSNARNANR TANAYNTCNG GRTA            44
```

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: Other
        (B) LOCATION: 11...29
        (D) OTHER INFORMATION: each N represents I (xi) SEQUENCE DESCRIPTION: SEQ ID NO:14:

ATGGATCCAT NATNGAYTGY MGNTWYCCNT AYGA          34

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: Other
        (B) LOCATION: 11...29
        (D) OTHER INFORMATION: each N represents I (xi) SEQUENCE DESCRIPTION: SEQ ID NO:15:

ATGGATCCAT NATNGAYTGY MGNTWYGANT AYGA          34

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:16:

TWYGARTAYM GNCAYGTNAT G          21

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:17:

AANARNARDA TRTGNGGYTC          20

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:18:

TCNGGNGCNC KRTACCANAR NGT          23

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:19:

```
GGNGARGGNA CNTAYGGNGT NGT                                                      23
```

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:20:

```
GANGANYKNG MNGANCCNYT NATG                                                     24
```

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:21:

```
ATNCKNCKNA RRAARTTCAT                                                          20
```

( 2 ) INFORMATION FOR SEQ ID NO:22:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:22:

```
GACCAACACG AATTCCAAAT GGTAGAGTTA TCTG                                          34
```

( 2 ) INFORMATION FOR SEQ ID NO:23:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:23:

```
TGAGGAGTCG ACCAAGATTT ATTGCATG                                                 28
```

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:24:

```
CATTTTGAAT TCATAGTAAT GCCACAAGTC                                               30
```

( 2 ) INFORMATION FOR SEQ ID NO:25:

```
( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:25:

ATAGTCCTCG AGACTTTACT CTTCTGCTTC                                          30
```